United States Patent
Goto

(10) Patent No.: US 8,326,013 B2
(45) Date of Patent: Dec. 4, 2012

(54) IMAGE PROCESSING DEVICE, IMAGE PROCESSING METHOD, AND IMAGE PROCESSING PROGRAM

(75) Inventor: Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 184 days.

(21) Appl. No.: 12/993,337

(22) PCT Filed: May 18, 2009

(86) PCT No.: PCT/JP2009/059119
§ 371 (c)(1),
(2), (4) Date: Nov. 18, 2010

(87) PCT Pub. No.: WO2009/145076
PCT Pub. Date: Dec. 3, 2009

(65) Prior Publication Data
US 2011/0069875 A1 Mar. 24, 2011

(30) Foreign Application Priority Data
May 28, 2008 (JP) .................................. 2008-139403

(51) Int. Cl.
*G06K 9/40* (2006.01)
(52) U.S. Cl. ........ 382/132; 382/131; 382/128; 382/172; 382/171; 382/173; 382/194; 382/260; 382/264; 382/255; 382/275; 382/300; 382/299; 382/298
(58) Field of Classification Search .................. 382/132, 382/128, 131, 228, 260, 298, 299, 300
See application file for complete search history.

(56) References Cited

U.S. PATENT DOCUMENTS

| | | | | | |
|---|---|---|---|---|---|
| 5,825,909 | A | * | 10/1998 | Jang ............................... | 108/173 |
| 5,915,036 | A | * | 6/1999 | Grunkin et al. ............... | 382/280 |
| 6,785,415 | B1 | | 8/2004 | Taguchi et al. | |
| 7,430,335 | B2 | * | 9/2008 | Dumitras et al. ....... | 348/E5.077 |
| 7,835,555 | B2 | * | 11/2010 | Kiraly et al. .................. | 382/131 |
| 2002/0054698 | A1 | * | 5/2002 | Ogino ........................... | 382/131 |
| 2002/0071600 | A1 | * | 6/2002 | Yamada ....................... | 382/264 |
| 2009/0116718 | A1 | * | 5/2009 | Goto et al. .................... | 382/131 |
| 2010/0272340 | A1 | * | 10/2010 | Bar-Aviv et al. ............. | 382/262 |

FOREIGN PATENT DOCUMENTS

| | | |
|---|---|---|
| JP | 63-209643 | 8/1988 |
| JP | 10-283471 | 10/1998 |
| JP | 2002-63574 | 2/2002 |
| JP | 2003-225234 | 8/2003 |
| JP | 2006-167187 | 6/2006 |
| JP | 2007-202916 | 8/2007 |

OTHER PUBLICATIONS

International Search Report in PCT/JP2009/059119.

* cited by examiner

*Primary Examiner* — Claire X Wang
*Assistant Examiner* — Chinenye Okafor
(74) *Attorney, Agent, or Firm* — Cooper & Dunham LLP

(57) ABSTRACT

A technique is disclosed for reducing noise in a medical image, wherein plural anisotropic areas continuous with a pixel-of-interest contained in the medical image are set with the pixel-of-interest being centered a statistical amount of pixel values of pixels constituting each anisotropic area is calculated with respect to each of the plural anisotropic areas, and either an anisotropic area having the minimum statistical amount out of the plural anisotropic areas is determined and an anisotropic shape filter in the same direction as the anisotropic area concerned is constructed, or an anisotropic area having the maximum statistical amount out of the plural anisotropic areas is determined and an anisotropic shape filter is constructed by clockwise or counterclockwise rotating the anisotropic area concerned around the pixel-of-interest by 90°.

12 Claims, 18 Drawing Sheets

F I G. 5
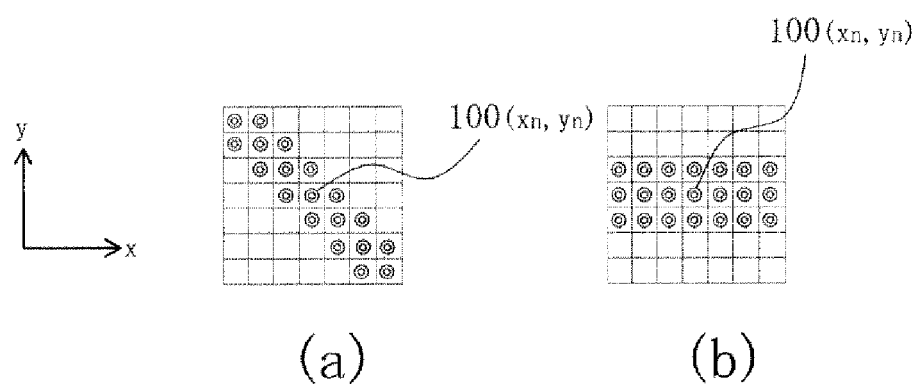

(a) ANISOTROPIC AREA — 111

| PIXEL COORDINATE | FIG.4 (b) | FIG.4 (c) | FIG.4 (d) | FIG.4 (e) | FIG.4 (f) | FIG.4 (g) | FIG.4 (h) | FIG.4 (i) |
|---|---|---|---|---|---|---|---|---|
| Xn, Yn | 20 | 30 | 40 | 20 | 20 | 50 | 30 | 40 |
| Xn+1, Yn | 20 | 20 | 60 | 80 | 40 | 90 | 80 | 100 |
| ... | | | | | | | | |
| Xn+100, Yn+100 | 20 | 20 | 40 | 30 | 50 | 30 | 40 | 40 |

(b) — 112

| PIXEL COORDINATE | maxSD | | FURTHER SD |
|---|---|---|---|
| Xn, Yn | FIG.4 (g) | 50 | 11.2 |
| Xn+1, Yn | FIG.4 (i) | 100 | 31.3 |
| ... | | | |
| Xn+100, Yn+100 | FIG.4 (f) | 50 | 10.6 |

IMAGE PROCESSING DEVICE, IMAGE PROCESSING METHOD, AND IMAGE PROCESSING PROGRAM

TECHNICAL FIELD

The present invention relates to an image processing device, an image processing method and an image processing program, and particularly to a technique of reducing image noise which is liable to occur in an X-ray CT image having a small irradiated X-ray dose or a magnetic resonance imaging image having a low magnetic field intensity.

BACKGROUND ART

Various image emphasis processing and noise reducing processing have been hitherto developed to enhance visibility of medical images. For example, Patent Document 1 discloses, as image emphasis processing, a technique of extracting a characteristic of each image portion and selecting a filter function corresponding to the characteristic to perform emphasis processing. Furthermore, Patent Document 2 discloses a technique of investigating the density gradation of points around a target point (=points in the neighborhood of the target point), calculating an average value of pixel values in the gradation maximum direction and emphasizing an image by using the average value when the target point is emphasized.

Furthermore, Patent Document 2 discloses a technique of separating an image into an edge portion and an flat portion and performing smoothing processing which is matched with the characteristic of each image portion.

PRIOR ART DOCUMENT

Patent Document
  Patent Document 1: JP-A-2006-167187
  Patent Document 2: JP-A-10-283471

SUMMARY OF THE INVENTION

Problem to be Solved by Invention

Patent Document 1 has a problem that high-frequency noise is also emphasized because it is a technique relating to image emphasis. Furthermore, Patent Document 2 has a description on noise reduction, however, it does not consider that a blood vessel has a running direction. Still furthermore, Patent Document 2 executes the smoothing processing corresponding to the characteristic of each of the edge portion and the flat portion, and thus has a problem that the calculation amount increases.

Furthermore, occurrence of noise is varied in accordance with an imaging condition, however, each of these Patent Documents leaves this point out of consideration.

The present invention has been implemented in view of the foregoing problems, and has an object to provide a noise reducing technique that is also effective particularly to a case where the running direction of a blood vessel is complicated (for example, blood vessels of lung field, etc.).

Means of Solving the Problem

In order to solve the problem, image processing device, method and program according to the present invention execute noise removing processing by using a filter whose shape corresponds to a partial characteristic of an image, thereby performing noise reducing processing which considers particularly the running direction of a blood vessel. The present invention originally relates to three-dimensional (over plural slices) processing, however, two-dimensional (within the same slice) processing will be described to simplify the description.

More specifically, an image processing device according to the present invention is characterized by comprising: image reading means that reads a medical image; anisotropic area setting means that sets plural anisotropic areas continuous with a pixel-of-interest contained in the medical image with the pixel-of-interest being centered; statistical amount calculating means that calculates a statistical amount of pixel values of pixels constituting each anisotropic area with respect to each of the plural anisotropic areas; filter setting means that determines an anisotropic area having the minimum statistical amount out of the plural anisotropic areas and constructs an anisotropic shape filter in the same direction as the anisotropic area concerned, or determines an anisotropic area having the maximum statistical amount out of the plural anisotropic areas and constructs an anisotropic shape filter by clockwise or counterclockwise rotating the anisotropic area concerned around the pixel-of-interest by 90°, and sets any one of the former anisotropic shape filter and the latter anisotropic shape filter; and filter processing means that performs median filter processing or smoothing filter processing by using the anisotropic shape filter.

The "pixel values" in this specification contain not only CT values of a CT image as an original image and the density values of an MRI image, US image, an XR image as original images, but also pixel values after these CT values, the density values are subjected to image processing such as gradation processing or the like.

[Median filer processing] is the processing of replacing the center value of pixel values of pixels constituting a filter with the pixel value of a pixel-of-interest.

[Smoothing processing] is the processing of replacing the average value of pixel values of pixels constituting a filter with the pixel value of a pixel-of-interest.

An image processing method according to the present invention is characterized by comprising: a step that reads a medical image; a step that sets plural anisotropic areas continuous with a pixel-of-interest contained in the medical image with the pixel-of-interest being centered; a step that calculates a statistical amount of pixel values of pixels constituting each anisotropic area with respect to each of the plural anisotropic areas; a step that determines an anisotropic area having the minimum statistical amount out of the plural anisotropic areas and constructs an anisotropic shape filter in the same direction as the anisotropic area concerned, or determines an anisotropic area having the maximum statistical amount out of the plural anisotropic areas and constructs an anisotropic shape filter by clockwise or counterclockwise rotating the anisotropic area concerned around the pixel-of-interest by 90°, and sets any one of the former anisotropic shape filter and the latter anisotropic shape filter; and a step that performs median filter processing or smoothing filter processing on the pixel-of-interest by using the anisotropic shape filter.

Furthermore, an image processing program according to the present invention is characterized by making a computer execute: a step that reads a medical image; a step that sets plural anisotropic areas continuous with a pixel-of-interest contained in the medical image with the pixel-of-interest being centered; a step that calculates a statistical amount of pixel values of pixels constituting each anisotropic area with respect to each of the plural anisotropic areas; a step that determines an anisotropic area having the minimum statistical amount out of the plural anisotropic areas and constructs an anisotropic shape filter in the same direction as the anisotropic area concerned, or determines an anisotropic area having the maximum statistical amount out of the plural anisotropic areas and constructs an anisotropic shape filter by clockwise or counterclockwise rotating the anisotropic area concerned around the pixel-of-interest by 90°, and sets any one of the former anisotropic shape filter and the latter anisotropic shape filter; and a step that performs median filter processing or smoothing filter processing on the pixel-of-interest by using the anisotropic shape filter.

Effect of the Invention

According to the present invention, noise can be reduced in consideration of the running direction of a blood vessel, and thus noise can be particularly effectively reduced even in a case where the running direction of a blood vessel is complicated (for example, blood vessels in lung field, etc.). Furthermore, noise can be reduced effectively to an image in which noise is increased due to an imaging condition.

BRIEF DESCRIPTION OF THE DRAWINGS

[FIG. 4] is a schematic diagram showing an example of an isotropic area and an anisotropic area, wherein
FIG. 4(a) shows the isotropic area and FIGS. 4(b) to (i) show examples of the anisotropic area.
[FIG. 5] is a schematic diagram showing another example of the anisotropic area.
[FIG. 11] is a schematic diagram showing examples of a standard deviation table and a reference standard deviation table.

MODES FOR CARRYING OUT THE INVENTION

Figure 1:
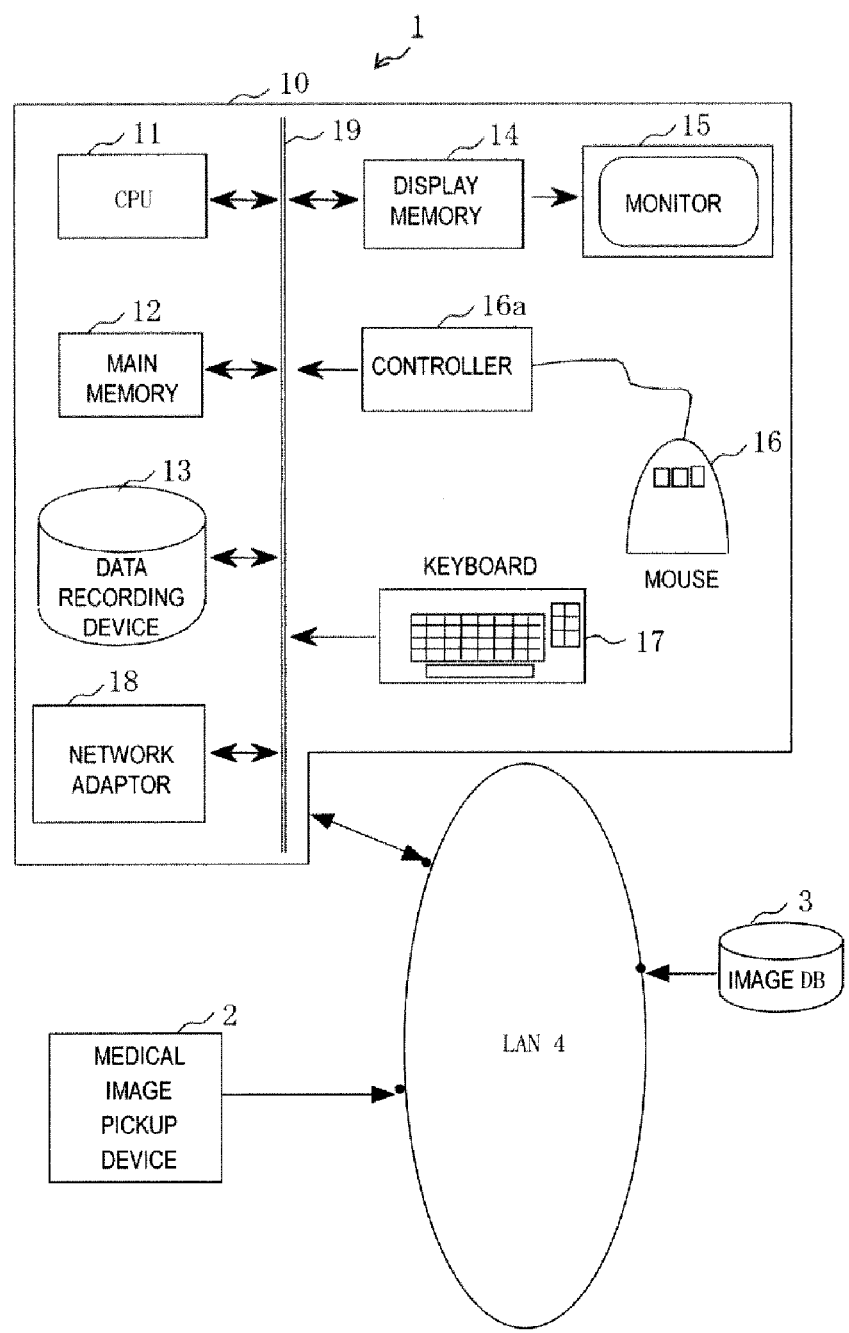
[FIG. 1] is a diagram showing the rough construction of an image processing system using an image processing device according to the present invention.

Preferred embodiments of an image processing device according to the present invention will be described hereunder with reference to the accompanying drawings. In all the figures, the elements having the same function are represented by the same reference numeral, and the repetitive description thereof is omitted.

FIG. 1 is a diagram showing the rough construction of an image processing system using an image processing device according to the present invention. An image processing system 1 is constructed by connecting, through LAN 4, a medical image pickup device 2 such as an X-ray CT device, a magnetic resonance imaging device (hereinafter referred to as "MRI device"), an ultrasonic device (hereinafter referred to as "US device"), an X-ray imaging device or the like disposed in a hospital or health checkup center, an image database (image DB) 3 for storing a medical image and an image processing device 10 to which the present invention is applied.

The image processing device 10 mainly includes a central processing unit (CPU) 11 for mainly controlling the operation of various constituent elements, a main memory 12, a data recording device 13, a display memory 14 for temporarily storing display data, an image display device 15 including a liquid crystal monitor, CRT or the like, a mouse 16 for operating a soft switch on the image display device 15, a pointing device (not shown) such as a track ball, a touch panel or the like, a controller 16a for the pointing device, a keyboard 17 having various parameter setting keys and switches, a network adaptor 18 for connecting the image processing device 10 to LAN 4, a telephone line, a network such as the Internet or the like, and a data bus 19 for connecting the respective constituent elements described above. The data recording device 13 may be a storing device such as a memory, a hard disk or the like which is internally or externally provided in the image processing device 10, a device for writing or reading data into/from a loadable external media or a device for transmitting/receiving data to/from an external storing device through a network.

Figure 2:
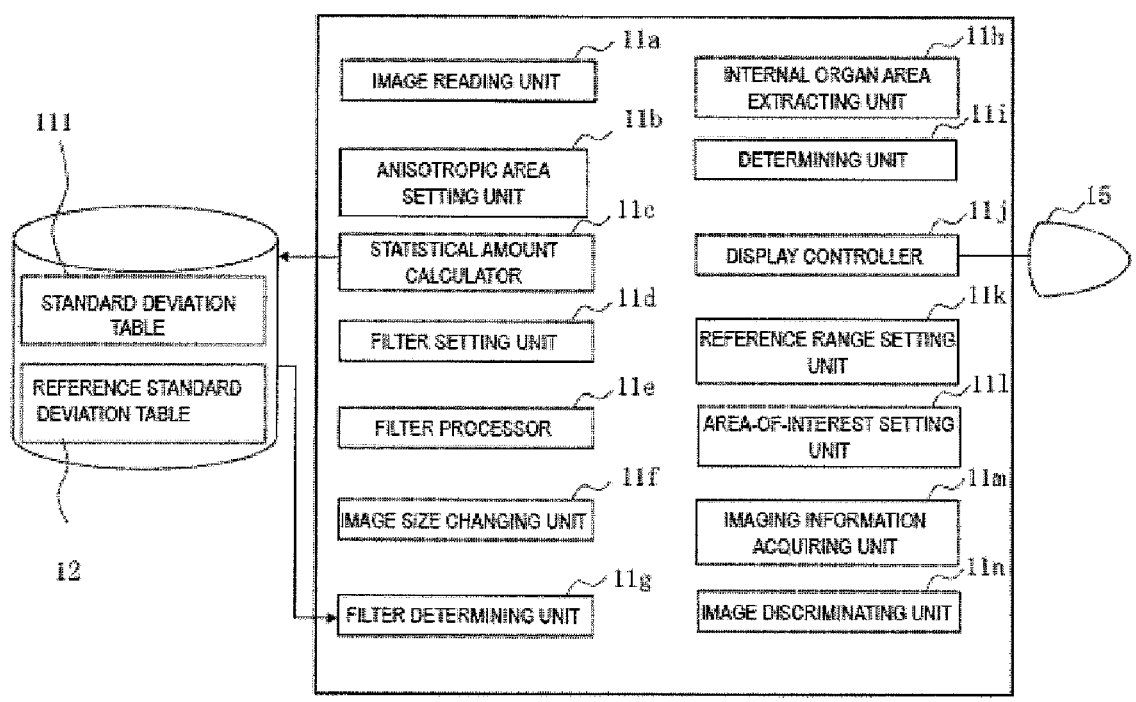
[FIG. 2] is a block diagram showing an image processing program.

FIG. 2 is a block diagram showing an image processing program installed in the image processing device 10.

The image processing program contains an image reading unit 11a for reading a medical image, an anisotropic area setting unit 11b for setting a plurality of anisotropic areas each comprising a pixel array having any shape continuous with a pixel-of-interest contained in the medical image with the pixel-of-interest being centered, a statistical amount calculator 11c for calculating a statistical amount of pixel values of pixels constituting each anisotropic area, a filter setting unit 11d for setting an anisotropic shape filter or isotropic shape filter, a filter processor 11e for performing median filter processing or smoothing filter processing, an image size changing unit 11f for enlarging/reducing the medical image, a filter determining unit 11g for determining whether the isotropic shape filter is applied to the pixel-of-interest, an internal organ area extracting unit 11h for extracting a target internal organ area from the medical image, a determining unit 11i for determining whether the maximum value of the statistical amount of the anisotropic area is within a predetermined reference range, a display controller 11j for controlling display of a histogram or a medical image on a monitor 15, a reference range setting unit 11k for setting various reference ranges, an area-of-interest setting unit 11l for setting an area-of-interest on the medical image, an imaging information acquiring unit 11m for acquiring imaging information of the medical image, and an image discriminating unit 11n for discriminating a medical image the imaging condition for which satisfies a predetermined condition.

The image reading unit 11a may receive and read the medical image from the medical image pickup device 2 or the image DB 3 through LAN 4, or read the medical image from the data recording device 13 provided to the image processing device 10. The image processing program is loaded into the main memory 12, and executed by CPU 11, whereby the program carries out the function.

In the following embodiments, a case where noise reducing processing is executed on an X-ray CT image obtained by imaging a region of chest of an examinee will be described. However, the medical image is not limited to an CT image, but may be an MRI image, a US image or an X-ray (roentgen) image. Furthermore, the imaging site is not limited to the region of chest, but the embodiments maybe effective to a medical image obtained by imaging an internal organ containing many hollow viscuses such as blood vessels or the like as in the case of a liver.

<First Embodiment>

This is an embodiment for changing a filter direction of a noise reducing filter. A first embodiment of the present invention will be described with reference to FIG. 3.

Figure 3:
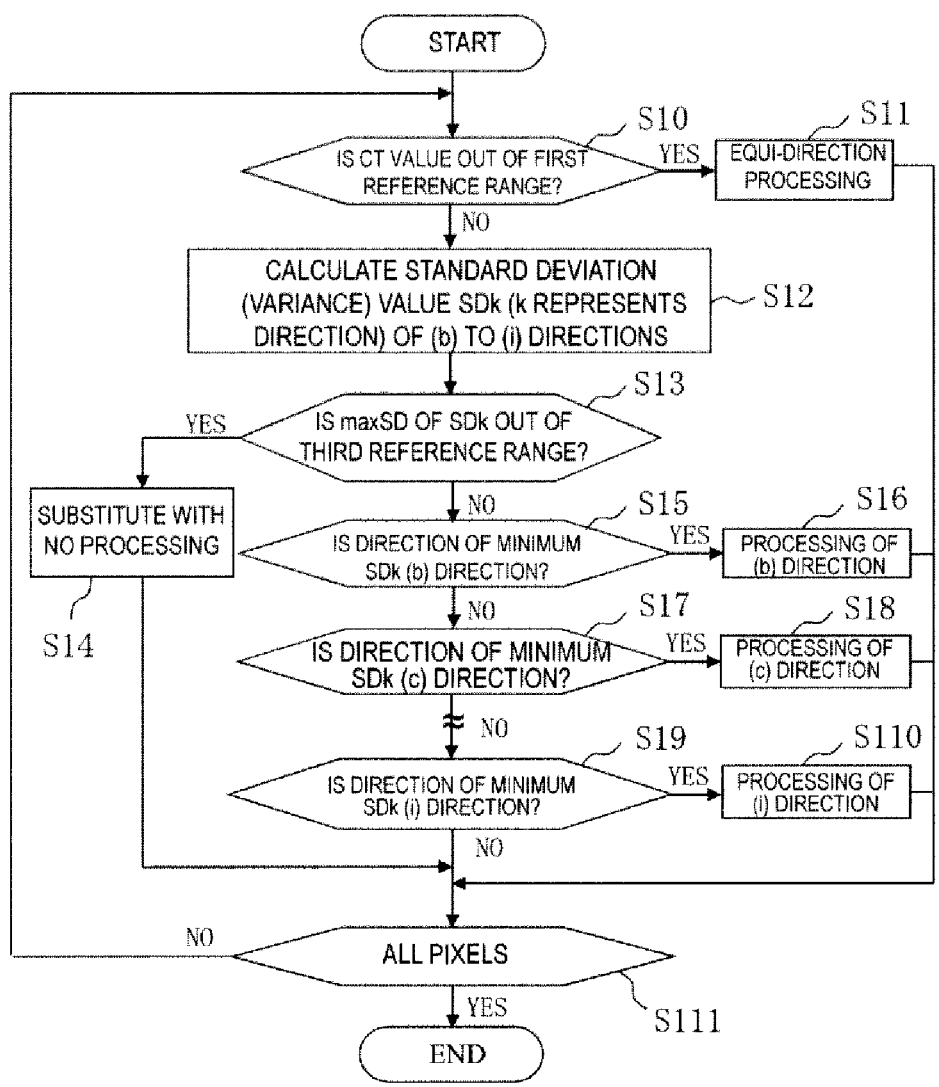
[FIG. 3] is a flowchart showing the flow of processing of a first embodiment.

FIG. 3 is a flowchart showing the flow of processing according to the first embodiment. In the first embodiment, noise reducing processing using an anisotropic shape filter is executed on only a lung field area in a CT image obtained by imaging a region of chest of an examinee. Therefore, the range of CT values (CT values=−1800 to −600) corresponding to the lung field area serving as a first reference range as a criterion for determining whether an isotropic shape filter is used or not is stored in the data storing device 13 of the image processing device 10 before the following processing.

Furthermore, a third reference range as a threshold value used in step S13 described later (in this embodiment, standard deviation 80 or more) is stored in the data storing device 13. When an anisotropic area is located over a blood vessel or at an edge portion, and the standard deviation tends to increase. Therefore, the third reference range is used to prevent collapse of blood vessels or blurring of edges when the noise reducing processing is executed on these areas.

The description will be made along a flowchart of FIG. 3. FIG. 3 is a flowchart showing the flow of processing according to the first embodiment.

(Step S10)

First, the image reading unit 11*a* reads a CT image. Subsequently, the filter determining unit 11*g* compares the CT value of a pixel-of-interest with a first reference range which is defined by CT values and used to determine whether an isotropic shape filter is used or not. In this embodiment, CT values of a lung field of an examinee (CT values=−1800 ∼−600) is stored as the first reference range in the data storing device 13. When the CT value of the pixel-of-interest is out of the first reference range, the processing goes to step S11, and when it is within the first reference range, the processing goes to step S12.

(Step S11)

The filter setting unit 11*d* sets an isotropic shape filter having a matrix shape of N×N having a pixel-of-interest located at the center. The filter processor 11*e* executes median filter processing on the pixel-of-interest by using the isotropic shape filter, whereby the processing in the isotropic direction is executed on the pixel-of-interest.

Figure 4:
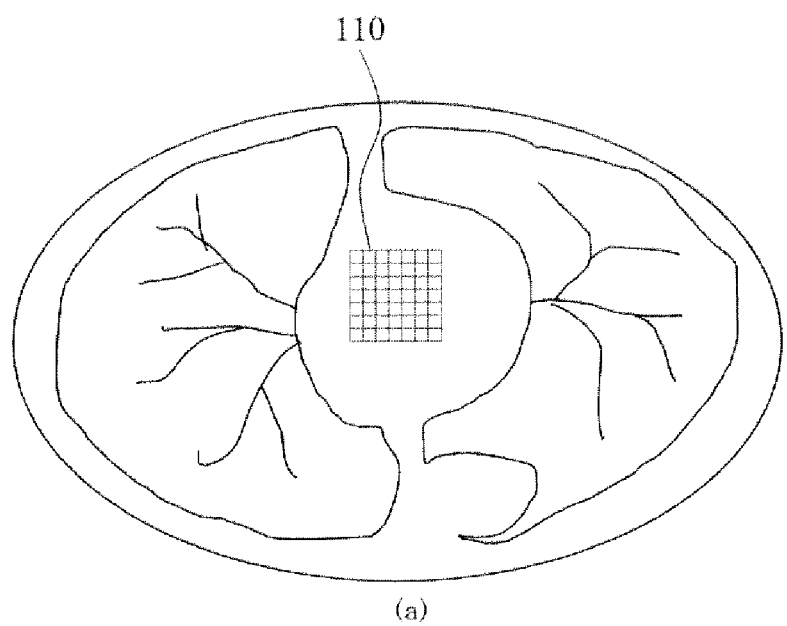
Figure 4:
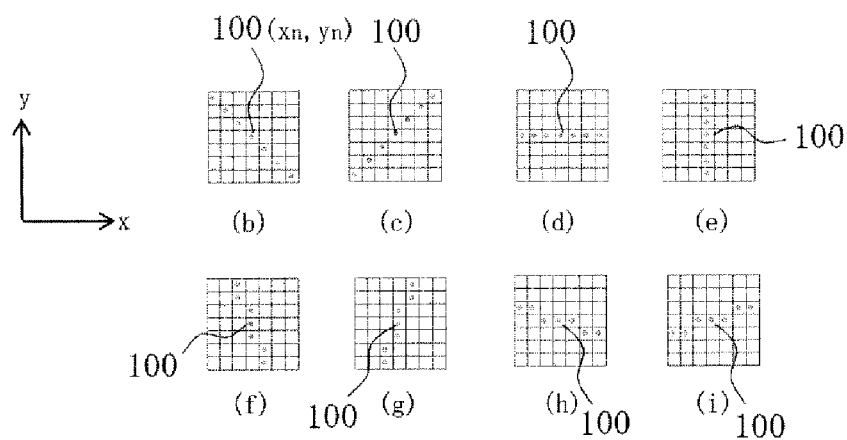

FIG. 4 is a schematic diagram showing examples of an isotropic area and an anisotropic area, and FIG. 4(*a*) shows a case where a filter 110 of a matrix size 7×7 is acted on the CT image. In this embodiment, for the purpose of noise reduction, a median filter is mainly adopted as a filter processing means, and the processing of arranging 49 pixels constituting the filter 110 in the decreasing (or increasing) order of pixel values, determining the center value of these pixels and adopting the value concerned as the pixel value of the pixel-of-interest is executed. When some blur is permitted to the processing result, a smoothing filter for calculating the average value of the pixel values of the 49 pixels in the filter 110 and adopting the average value concerned as the pixel value of the pixel-of-interest may be used.

(Step S12)

The anisotropic area setting unit 11*b* sets plural anisotropic (also called as anisotropic) areas with a pixel-of-interest 100 being centered. The statistical amount calculator 11*c* calculates the statistical amount of each set anisotropic area.

In this embodiment, eight kinds of anisotropic areas of FIGS. 4(*b*) to (*i*) are set. The anisotropic area is defined as an area which contains a pixel-of-interest at the center thereof and is continuous in any direction with the pixel-of-interest being centered in an N×N area. In other words, the anisotropic area is a pixel array which has any shape other than the matrix shape of N×N and is continuous with the pixel-of-interest being located at the center thereof in the N×N area containing the pixel-of-interest.

Examples of the anisotropic area will be described with reference to FIGS. 4(*b*) to (*i*) and FIGS. 5(*a*) (*b*). Each of the anisotropic areas shown in FIGS. 4(*b*) to (*i*) is constructed by 1×7 (1 may stride over plural lines or columns) pixels continuous with the pixel-of-interest 100 in an area of 7×7 containing the pixel-of-interest 100 located at the center thereof. In the figures, it is constructed by seven circled pixels.

FIG. 4(*b*) shows an example of the anisotropic area comprising a pixel array of 1×7 pixels continuous on a diagonal line extending from the upper left side to the lower right side with the pixel-of-interest 100 being centered. FIG. 4(*c*) shows an example of the anisotropic area comprising a pixel array of 1×7 pixels continuous on a diagonal line extending from the lower left side to the upper right side with the pixel-of-interest 100 being centered. FIG. 4(*d*) shows an example of the anisotropic area comprising a pixel array of 1×7 pixels continuous on a straight line in a lateral direction (X-axis direction) with the pixel-of-interest 100 being centered. FIG. 4(*e*) shows an example of the anisotropic area comprising a pixel array of 1×7 pixels continuous on a straight line in a longitudinal direction (Y-axis direction) with the pixel-of-interest 100 being centered. Pixels arranged on a line as described above may be used as the anisotropic area, however, pixels arranged in any shape as described below may be used.

For example, FIG. 4(*f*) shows an example of the anisotropic area including totally seven pixels of two pixels (Xn, Yn−1), (Xn, Yn+1) adjacent to the pixel-of-interest 100 (Xn, Yn) in the longitudinal direction, two pixels (Xn−1, Yn+2), (Xn+1, Yn−2) adjacent to both of these two pixels in a slant direction, and two pixels (Xn−1, Yn+3), (Xn+1, Yn−3) adjacent to both of these two pixels in the longitudinal direction.

FIG. 4(*g*) shows an example of the anisotropic area including totally seven pixels of two pixels (Xn, Yn−1), (Xn, Yn+1) adjacent to the pixel-of-interest 100 (Xn, Yn) in the Y-axis direction, two pixels (Xn−1, Yn−2), (Xn+1, (Xn+1, Yn+2) adjacent to both of these pixels in a slant direction, and further two pixels (X−1, Yn−3), (Xn+1, Yn+3) adjacent to both of these pixels in the longitudinal direction.

FIG. 4(*h*) shows an example of the anisotropic area including totally seven pixels of two pixels (Xn−1, Yn), (Xn+1, Yn) adjacent to the pixel-of-interest 100 (Xn, Yn) in the lateral direction, two pixels (Xn−2, Yn+1), (Xn+2, Yn−1) adjacent to both of these pixels in a slant direction, and further two pixels (Xn−3, Yn+1), (Xn+3, Yn−1) adjacent to both of these pixels in the lateral direction.

FIG. 4(*i*) shows an example of the anisotropic area comprising totally seven pixels of two pixels (Xn−1, Yn), (Xn+1, Yn) adjacent to the pixel-of-interest 100 (Xn, Yn) in the lateral direction, two pixels (Xn−2, Yn−1), (Xn+2, Yn+1) adjacent to both of these pixels in a slant direction and further two pixels (Xn−3, Yn−1), (Xn+3, Yn+1) adjacent to both of these pixels in the lateral direction.

In the foregoing description, the anisotropic area is constructed by using pixels arranged in the form of 1×N. However, the anisotropic area maybe constructed by using n (<N) columns and/or lines in the N×N area and thus constructed by pixels of n×N.

FIG. 5 shows an example of use of three columns in a 7×7 area as an example of the anisotropic area comprising pixels of n×N.

FIG. 5(a) shows an anisotropic area which is continuous with the pixel-of-interest 100 (Xn, Yn) in a slant direction from the upper left side to the lower right side (includes totally 19 pixels of two pixels on a first line: (Xn−3, Yn+3), (Xn−2, Yn+3), three pixels on a second line: (Xn−3, Yn+2), (Xn−2, Yn+2), (Xn−1, Yn+2), three pixels on a third line: (Xn−2, Yn+1), (Xn−1, Yn+1), (Xn, Yn+1), three pixels on a fourth line: (Xn−1, Yn), (Xn, Yn), (Xn+1, Yn), three pixels on a fifth line: (Xn, Yn−1), (Xn+1, Yn−1), (Xn+2, Yn−1), three pixels on a sixth line: (Xn+1, Yn−2), (Xn+2, Yn−2), (Xn+3, Yn−2), and two pixels on a seventh line: (Xn+3, Yn−3), (Xn+2, Yn−3).

FIG. 5(b) shows an anisotropic area including totally 21 pixels of 3×7 pixels located on fourth to sixth lines with respect to the pixel-of-interest 100 (Xn, Yn).

In this embodiment, the anisotropic area setting unit 11b sets eight kinds of anisotropic areas shown in FIGS. 4(b) to (i), and the statistical amount calculator 11c obtains standard deviations of pixel values of each anisotropic area SD(b), SD(c), SD(d), SD(e), SD(f), SD(g), SD(h), SD(i) (hereinafter referred to as "SDk" (k represents the direction corresponding to b to i)).

In the foregoing description, the standard deviation SDk (k represents the direction) is obtained as a statistical amount, however, a variance may be obtained.

(Step S13)

The determining unit 11i compares the maximum value maxSD out of the eight standard deviations SDk calculated in step S12 with a third reference range recorded in the data recording device 13, and determines whether maxSD is out of the third reference range. In case of YES, the processing goes to step S14, and in case of NO, the processing goes to step S15.

(Step S14)

When MaxSD is out of the third reference range, the filter setting unit 11d substitutes the pixel value (CT value or density value) of the pixel-of-interest as the pixel value of a filter-processed image without setting any filter.

(step S15)

The filter setting unit 11d searches the minimum value out of the eight standard deviations SDk calculated in step S12, and determines whether the minimum value of SDk is equal to SD(b). In case of YES, the processing goes to step S16, and in case of NO, the processing goes to step S17.

(Step S16)

The filter setting unit 11d sets an anisotropic shape filter in the same direction as the anisotropic area of FIG. 4(b) with respect to the pixel-of-interest 100, and the filter processor 11e performs the median filter processing by using the anisotropic shape filter concerned.

Figure 6:
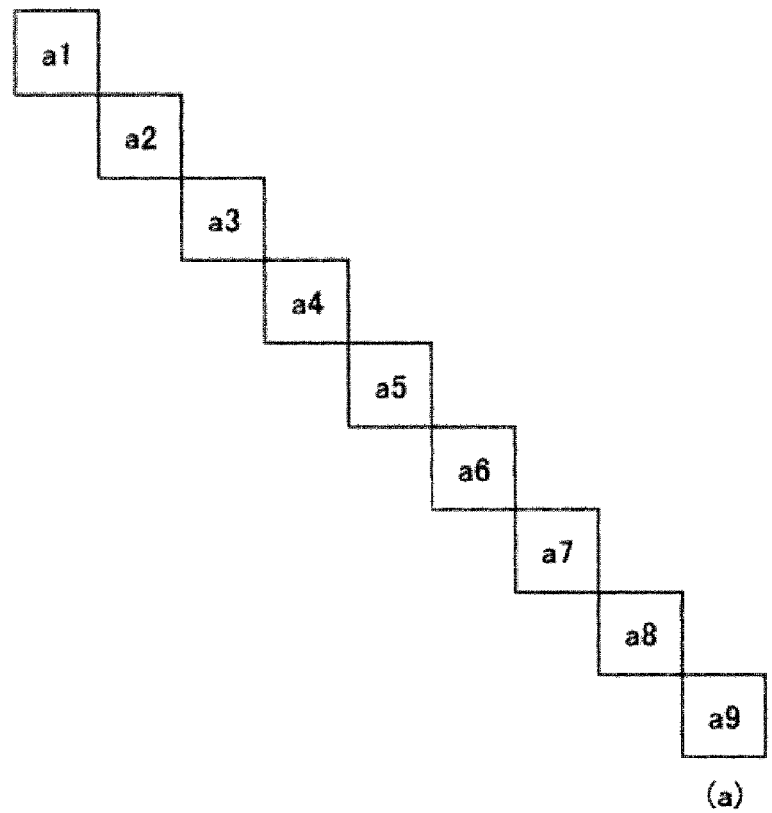
[FIG. 6] is a schematic diagram showing the processing contents of a median filter and a smoothing filter.
Figure 6:
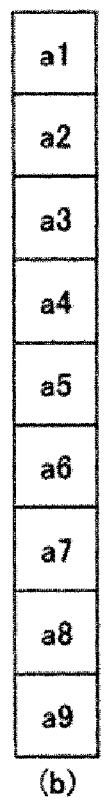

FIGS. 6(a) (b) are schematic diagrams showing the processing contents of the median filter and the smoothing filter. A 1×9 array filter including nine pixels of pixels a1 to a9 continuous from the upper left side to the lower right side with respect to a pixel-of-interest a5 is set in FIG. 6(a), and a 1×9 array filter including nine pixels of pixels a1 to a9 continuous in the up-and-down direction with respect to the pixel-of-interest a5 is set in FIG. 6(b).

For the purpose of noise reduction, the median filter is more preferable, and thus the filter processor 11e calculates center values of the pixels a1 to a9 in this embodiment. However, when the smoothing processing is performed in place of the median filter processing, the filter processor 11e may calculate the average value of the pixels a1 to a9 as a low pass filter.

(Step S17 to Step S110)

In step S17, as in the case of step S15, the filter setting unit 11d searches the minimum value out of the eight standard deviations SDk calculated in step S12 and determines whether the minimum value of SDk is equal to SD(c) or not. In case of YES, the processing goes to step S18. In step S18, as in the case of the step S16, the filter setting unit 11d sets an anisotropic shape filter in the same direction as the anisotropic area of FIG. 4(c), and the filter processor 11e performs the median filter processing by using the filter concerned. It is necessary that the direction of the anisotropic shape filter is the same as the direction of the anisotropic area, however, the length (size) of the anisotropic shape filter may be different from the length (size) of the anisotropic area.

The same processing as the steps S15 and S16 is executed on the five directions from FIGS. 4(d) to 4(h) although it is omitted from the drawings.

In step S19 and step S110, the same processing as the step S15 and the step S16 is executed on the final anisotropic area on which the processing of the step S15 and the step S16 out of the plural statistical amounts obtained in FIG. 4(i), that is, in the step S12 has not yet been completed.

(step S111)

It is determined whether the processing is completed on all the pixels of the medical image. In case of YES, the processing is finished, and in case of NO, the processing returns to step S10.

According to this embodiment, a specific site (for example, a lung field area in a chest tomogram) of an examinee is specified on the basis of the CT value of a pixel-of-interest, and noise reducing processing using an anisotropic shape filter or noise reducing processing using an isotropic shape filter can be performed in accordance with the site concerned. Particularly, with respect to an area in which many blood vessels are imaged like a lung field area, noise reducing processing along the running of the blood vessels can be performed. Therefore, noise reduction can be performed while preventing erroneous breaking of a thin blood vessel area due to the noise reducing processing.

In the above embodiment, the number of anisotropic areas is set to eight of FIGS. 4(b) to 4(i). However, when the image size is larger, the number of anisotropic areas (the number of directions of the anisotropic areas) increases. Conversely, when the image size is smaller, the number of anisotropic areas may be reduced.

<Second Embodiment>

A second embodiment is an embodiment for changing the filter direction and the filter size at the same time. In the first embodiment, the anisotropic area is described as an area which has a size of n×7 (n<7) and includes a pixel array having any shape which is continuous with a pixel-of-interest. However, the filter size may be changed in connection with enlargement/reduction of an image or the smallness/largeness of FOV (Field of view).

Figure 7:
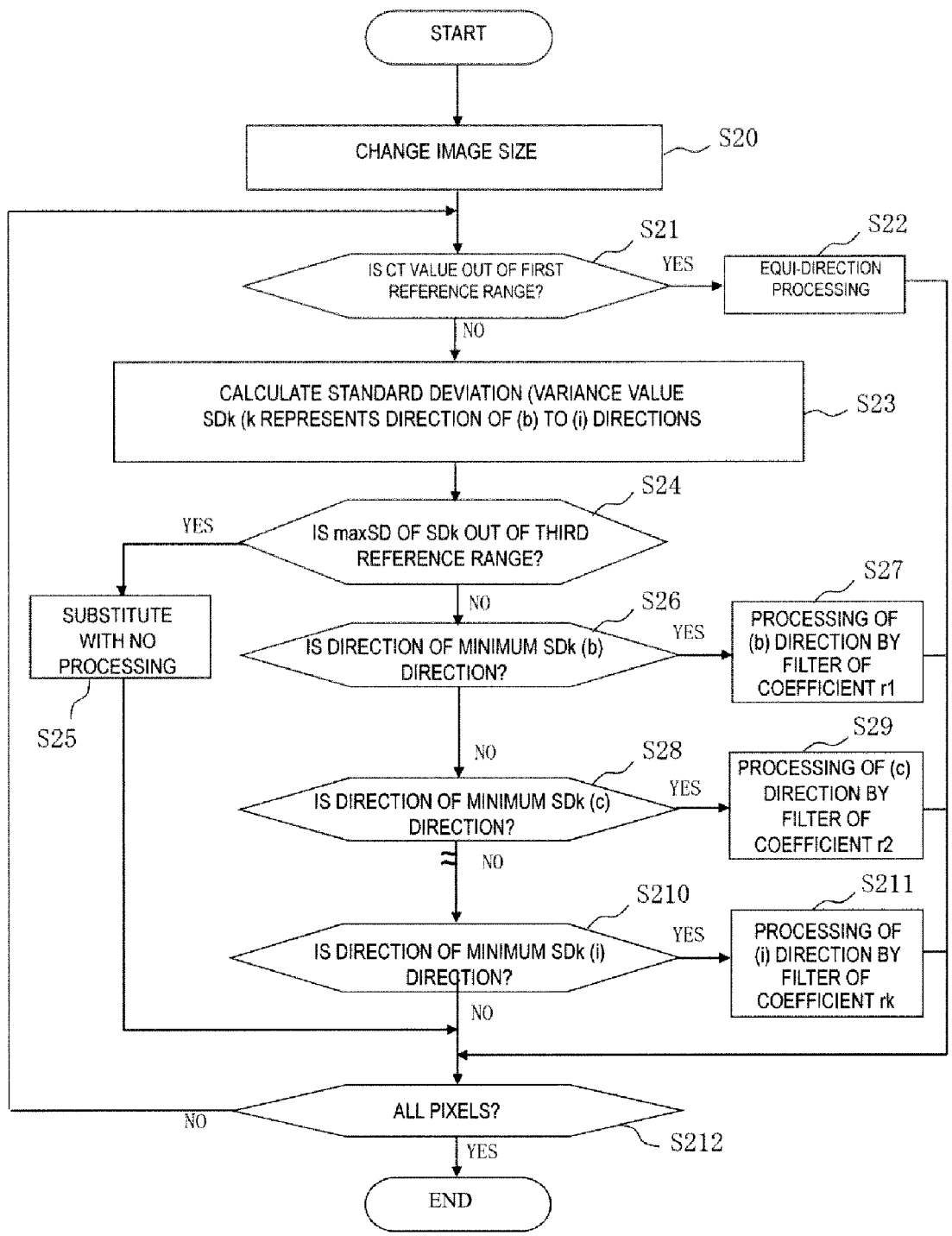
[FIG. 7] is a flowchart showing the flow of processing of a second embodiment.

The flow of processing according to the second embodiment will be described with reference to FIG. 7. FIG. 7 is a flowchart showing the flow of the processing according to the second embodiment.

Before the following processing, a function or table for determining a coefficient r to change the filter size in accordance with the magnification R representing an enlarging/reducing scale of the image size (H×W) or the smallness/largeness of FOV is stored in the data storing device 13 of the image processing device 10. The coefficient r is a coefficient which is not less than 0 and not more than 1. It has a larger value as the magnification R increases, and also it has a smaller value as the magnification R decreases.

When the Height and Width ratio (H:W) is changed, the coefficient r may be changed in accordance with the direction of each anisotropic area. For example, when an original image is enlarged at four times (twice in each of Height and Width, R=4), the coefficient r is set to 0.5 in the lateral direction and the longitudinal direction.

Furthermore, when equi-magnification processing is executed on an original image in the longitudinal direction while twice enlargement processing is executed on the original image in only the lateral direction, with respect to a filter having the same direction as the anisotropic area shown in FIG. 4(d) (an array of pixels arranged linearly in the lateral direction), the filter may be set by using r=1, and with respect to a filter having the same direction as the anisotropic area shown in FIG. 4(c) (an array of pixels arranged linearly in the longitudinal direction), the filter may be set by using r=0.

(Step S20)

When a user inputs a desired image size, the image size changing unit 11f performs the enlarging/reducing processing on a medical image by using the magnification R which is matched with the input value.

(Step S21 to Step S25)

Step S21 to step S25 execute the same processing as the step S10 to the step S14 of the first embodiment.

(Step S26)

The filter setting unit 11d refers to the data storing device 13, and determines the coefficient r1 on the basis of the enlargement scale R of the image and the direction of the anisotropic area of FIG. 4(b). Then, an anisotropic shape filter having the filter size determined by using the coefficient r1 is set.

Figure 8:
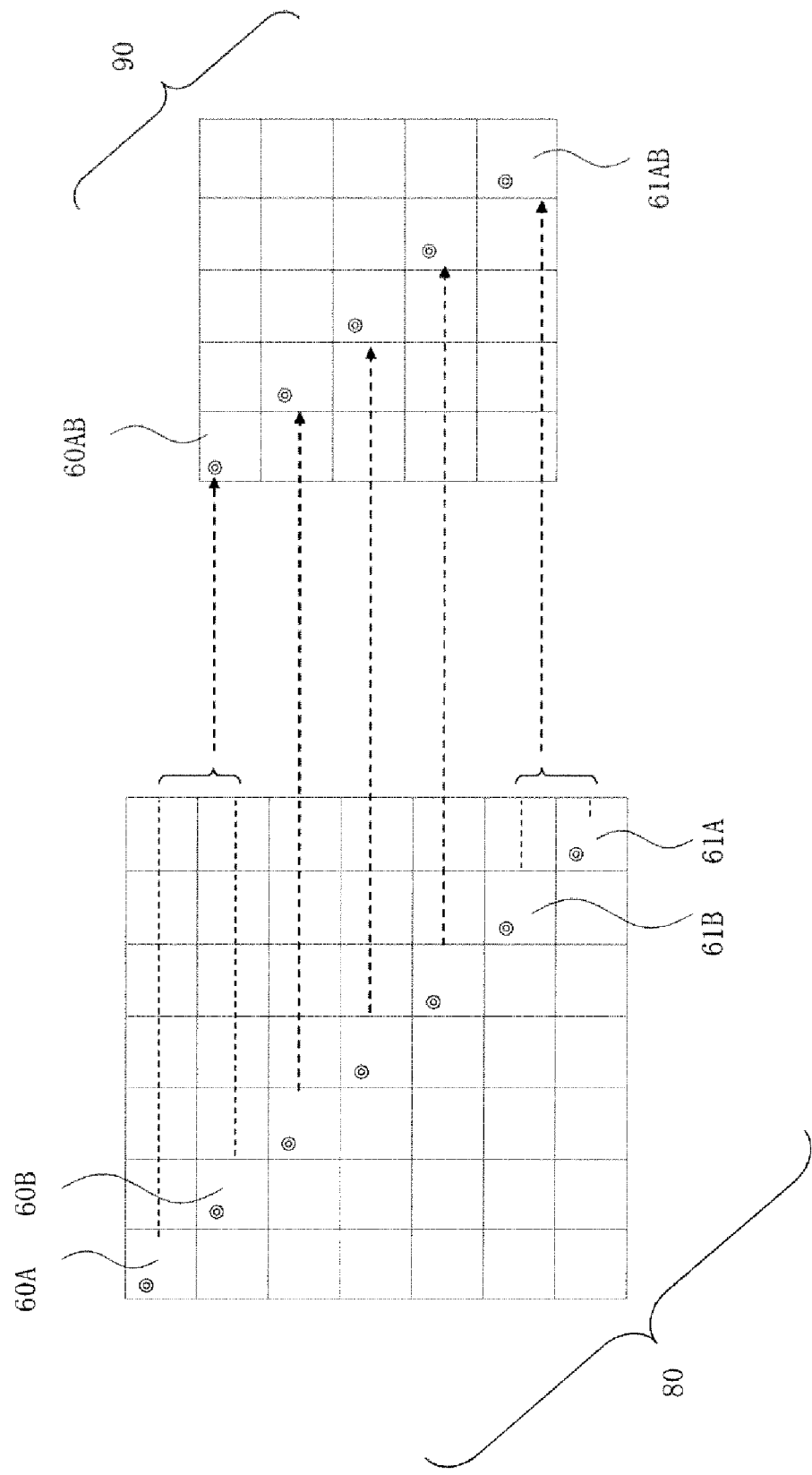
[FIG. 8] is a schematic diagram showing the processing of changing a filter size.

The processing of changing the filter size will be described with reference to FIG. 8. FIG. 8 is a schematic diagram showing the processing of changing the filter size, and an anisotropic area 80 of FIG. 8 is the same anisotropic area as shown in FIG. 4(b) with the pixel-of-interest 100 being centered. The filter setting unit 11d interpolates a pixel value 60A of a pixel (Xn−3, Yn+3) located at the left upper end portion of the anisotropic area 80 including seven pixels of 1×7, and a pixel value 60B of a pixel (Xn−2, Yn+2) adjacent to the above pixel according to the following mathematical expression by using the coefficient r1 described above, thereby calculating a pixel value 60AB.

$$60AB = r1 \cdot 60A + (1-r1) \cdot 60B \quad (1)$$

Likewise, the filter setting unit 11d subjects a pixel value 61A of a pixel (X+3, Yn−3) located at the right lower end portion of this pixel array, a pixel value 61B of a pixel (Xn+2, Yn−2) adjacent to the pixel (Xn+3, Yn−3) and the above coefficient r1 to weighted addition according to the following mathematical expression, thereby calculating a pixel value 61AB.

$$61AB = r1 \cdot 61A + (1-r1) \; 61B \quad (2)$$

According to the above mathematical expressions (1), (2), when the enlargement scale R of the image is relatively large, the contribution rate of the pixel located at the end portion of the anisotropic area can be increased. By using these calculation values, the filter setting unit 11d sets a filter including five pixels in which the number of pixels constituting the overall filter is smaller than seven pixels of the anisotropic area 80 by two pixels. The filer 90 uses the pixel values of the anisotropic area for the pixel-of-interest 100 and both the pixels adjacent to the pixel-of-interest 100, and also uses the calculation values 60AB and 61AB for the pixel values of the pixels at the end portions.

As described above, the pixel values of the pixels at both the end portions of the filter 90 are created according to the interpolation from the pixel values of the anisotropic area and the pixel values of the pixels which are adjacent to the above pixels and within the anisotropic area, whereby the filter size can be substantially set to any size irrespective of the number (integer times) of the pixels.

(Step S27)

The filter processor 11e sorts the pixel values of the set anisotropic shape filter 90 in the decreasing or increasing order of the pixel value, obtains the median value thereof and sets the value concerned as the pixel value of the pixel-of-interest 100.

(Step S28 to Step S211)

In step S28, as in the case of the step S26, the filter setting unit 11d determines whether the statistical amount of the anisotropic area shown in FIG. 4(c) is the minimum value or not, and in case of YES, the processing goes to step S29. In step S29, as in the case of the step S27, the filter setting unit 11d determines the coefficient r2 corresponding to the direction of the anisotropic area and the magnification R, and sets a filter using the coefficient r2, and the filter processor 11e performs the filter processing in the direction of the anisotropic area shown in FIG. 4(c) by using the filter.

With respect to the six directions from FIG. 4(d) to FIG. 4(i), the same processing as the steps S26 and S27 is executed.

(Step S212)

It is determined whether the processing has been completed with respect to all the pixels of the medical image. In case of YES, the processing is finished, and in case of NO, the processing returns to step S21.

According to this embodiment, the conventional filter has been hitherto constructed as an isotropic shape filter having a matrix shape of (2N+1)×(2N+1) (N: natural number) in filter size, and thus a filter having the next largest size to (2N+1)×(2N+1) is limited to {2(N+1)+1}×{2(N+1)+1}. For example, the filter size is limited like a 5×5 filter is next to a 3×3 filter and a 7×7 filter is next to the 5×5 filter. According to this embodiment, a filter having a filter size reflected to any pixel number which is not less than (2N+1) and not more than {2(N+1)+1} can be constructed in accordance with the enlarging/reducing scale of the image size.

In addition, according to this embodiment, the filter size may be changed in conformity with the image size, the size of FOV and the direction of the anisotropic area, and thus noise can be more effectively reduced.

In step S22, the equi-direction processing is executed by using the isotropic shape filter having the matrix shape of 7×7. However, the filter setting unit 11d may calculate the pixel values of the pixels located at the end portions and the pixel values of the pixels located at the just inside positions from the former pixels according to the mathematical expression (1) or the mathematical expression (2) by using the coefficient r0 corresponding to the magnification R, thereby interpolating and generating an isotropic shape filter having any size which is smaller than that of 7×7 and larger than that of 5×5, and the equi-direction processing may be performed by using the isotropic shape filter.

<Third Embodiment>

Figure 9:
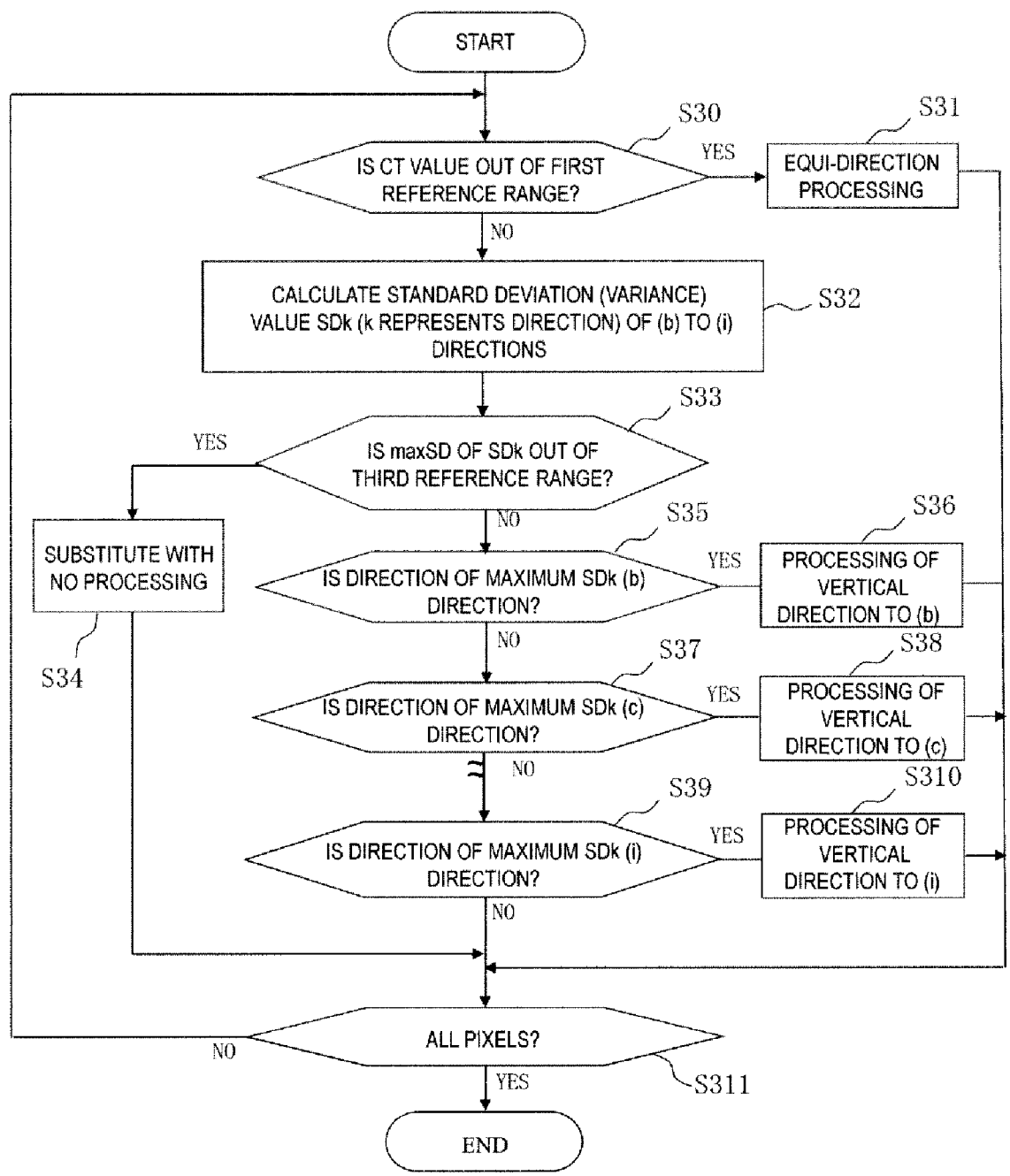
[FIG. 9] is a flowchart showing the flow of processing of a third embodiment.

This embodiment is an opposite approach to the first embodiment. In the step S15 to step S110 of FIG. 3 described above, the minimum value of the standard deviation is calculated, and the anisotropic shape filter in the same direction as the anisotropic area having the minimum value is set. On the other hand, in this embodiment, an anisotropic area whose standard deviation is the maximum value is detected, and a filter is set in the vertical direction to the direction of the anisotropic area. The flow of the processing of the third embodiment will be described with reference to FIG. 9. FIG. 9 is a flowchart showing the flow of the processing of the third embodiment. It is also assumed in this embodiment that the eight anisotropic areas shown in FIGS. 4(b) to 4(i) are set.

(Step S30 to Step S34)

The steps S30 to S34 execute the same processing from the step S10 to the step S14 of the first embodiment.

(Step S35)

The filter setting unit 11d searches the maximum value out of the eight standard deviations SDk calculated in step S32, and determines whether the maximum value of SDk is SD(b) or not. In case of YES, the processing goes to step S36, and in case of NO, the processing goes to step S37. When max SD is calculated in step S33, information on the direction of the anisotropic area may be acquired and diverted to the search of the maximum value.

(Step S36)

The filter setting unit 11d sets an anisotropic shape filter whose direction is identical to a direction when the anisotropic area of FIG. 4(b) is clockwise or counterclockwise rotated around the pixel-of-interest 100 by 90°. The filter processing unit 11e performs the same filter processing as the step S16 by using the anisotropic shape filter concerned, whereby the processing in the vertical direction to that of FIG. 4(b) is executed.

For example, a filter including seven pixels continuous from the upper right side to the lower left side in which the coordinate of the pixel located at the right upper end portion is (Xn+3, Yn+3) and the coordinate of the left lower end portion is (Xn−3, Yn−3) is set to the anisotropic area of FIG. 4(b) with the pixel-of-interest 100 being centered.

(Step S37 to Step S310)

In step S37, as in the case of the step S35, the filter setting unit 11d searches the maximum value out of the eight standard deviations SDk calculated in step S32, and determines whether the maximum value of SDk is SD(c) or not. In case of YES, the processing goes to step S38. In step S38, as in the case of the step S36, the filter setting unit 11d sets an anisotropic shape filter along the vertical direction to the direction of the anisotropic area of FIG. 4(c), and the filter processing unit 11 performs the filter processing by using the anisotropic shape filter concerned. The same processing as the steps S35 and S36 (not shown) is also executed on five directions from FIG. 4(d) to FIG. 4(h).

In steps S39, S310, the same processing as the steps S35 and S36 is performed on the last anisotropic area for which the processing of the step S35 and the step S36 has not yet been finished out of plural statistical amounts obtained in step S32.

(Step S311)

It is determined whether the processing has been completed on all the pixels of the medical image. In case of YES, the processing is finished, and in case of NO, the processing returns to step S30.

According to this embodiment, as in the case of the first embodiment, a specific site of the examinee (a lung field area in a chest tomogram, for example) is specified on the basis of the CT value of the pixel-of-interest, and the noise reducing processing using the anisotropic area or the noise reducing processing using the matrix shape can be performed in accordance with the site concerned. Particularly, the noise reducing processing along the running of blood vessels can be performed on an area for which many blood vessels are imaged as in the case of a lung field area, and thus the noise reduction can be performed while preventing thin blood vessels from being erroneously deleted by the noise reduction processing.

<Fourth Embodiment>

Figure 10:
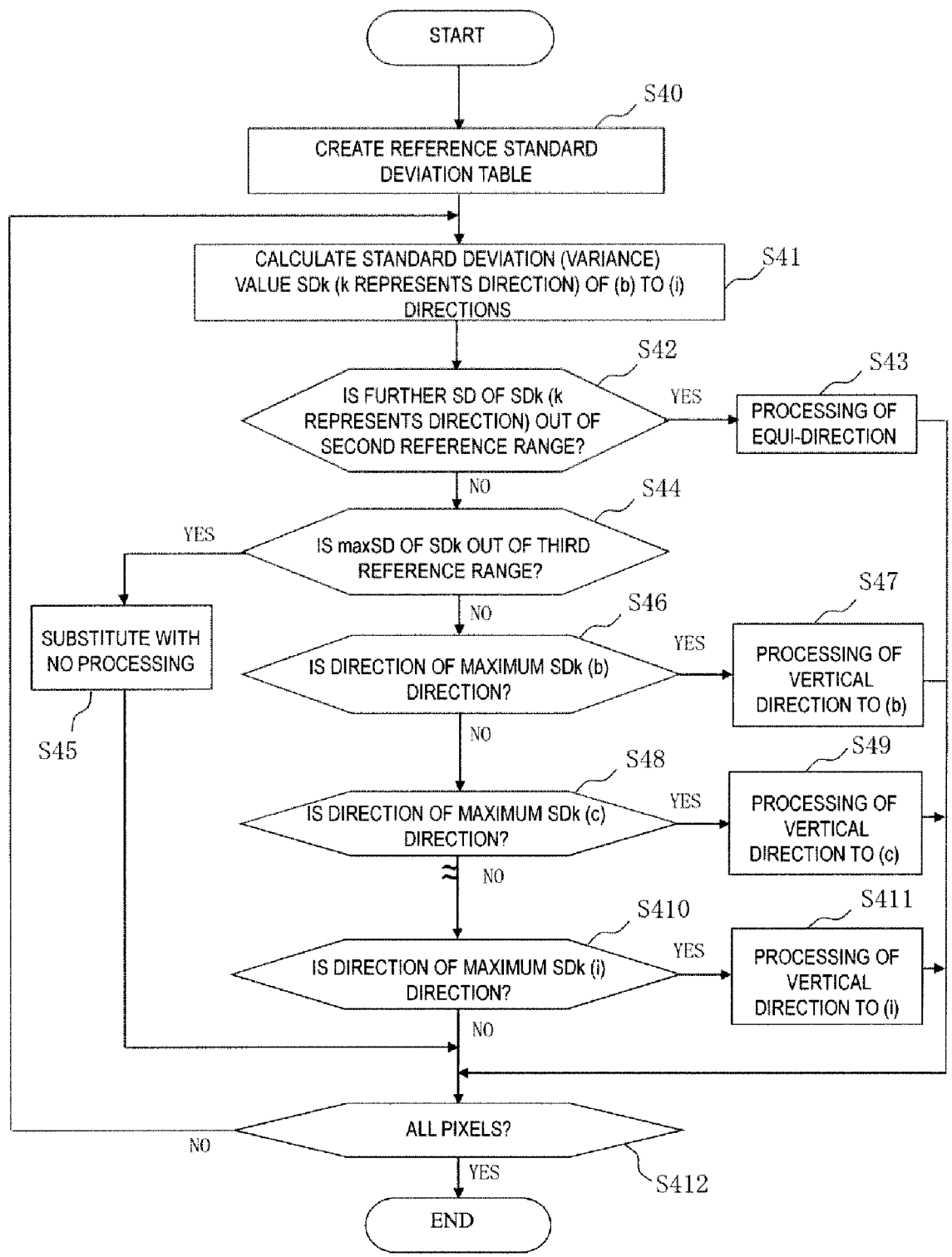
[FIG. 10] is a flowchart showing the flow of processing of a fourth embodiment.

A fourth embodiment is an embodiment for calculating standard deviations of plural anisotropic areas every pixel. The fourth embodiment will be described hereunder with reference to FIG. 10. FIG. 10 is a flowchart showing the flow of processing of the fourth embodiment.

Before the main processing, a second reference range used in step S42 described later is stored in the data recording device 13. This second reference range is a reference range defined by using a further standard deviation of the plural standard deviations obtained from the plural anisotropic areas, and used to determine whether the isotropic shape filter is used or not. Furthermore, the third reference range used in step S44 is also stored.

(Step S40)

With respect to all the pixels of the original image, the anisotropic area setting unit 11b sets the eight anisotropic areas shown in FIGS. 4(b) to 4(d), and the statistical amount calculator 11c calculates the standard deviation of the pixel values of the anisotropic area set every pixel. Furthermore, the statistical amount calculator 11c calculates the maximum value out of the plural standard deviations calculated every pixel and the further standard deviation (hereinafter referred to as "further SD") for which the plural standard deviations set for one pixel-of-interest are set as a population. The statistical amount calculator 11c generates a reference standard deviation table in which the maximum value and the further SD are stored, and stores the reference standard deviation table into the main memory 12 or the data storing device 13.

FIG. 11 shows an example of the standard deviation table. FIG. 11(a) shows a standard deviation table 111 in which the standard deviation of the plural anisotropic areas set every pixel is stored, and FIG. 11(b) shows a reference standard deviation table 112 generated on the basis of the standard deviation of FIG. 11(a). The direction and maximum value of the anisotropic area whose standard deviation is the maximum value (maxSD) with respect to each pixel, and the further SD are stored in the reference standard deviation table 112.

(Step S41)

The filter determining unit 11g refers to the value of "further SD" corresponding to the pixel-of-interest 100 of the reference standard deviation table 112 of FIG. 11.

(Step S42)

The filter determining unit 11g determines whether the "further SD" of the pixel-of-interest is out of the second reference range or not. When it is out of the second reference range, the processing goes to step S43, and when it is within the second reference range, the processing goes to step S44.

(Step S43)

The filter setting unit 11d sets the isotropic shape filter having the matrix shape of N×N with the pixel-of-interest being centered, and the filter processor 11e performs the median filter processing of replacing the pixel value of the pixel-of-interest with the center value of the pixel values of pixels constituting the set filter, whereby the equi-direction processing is executed on the pixel-of-interest.

(Step S44)

The determining unit 11*i* acquires the maximum value maxSD out of the standard deviations SDk of the eight anisotropic areas set with respect to the pixel-of-interest by referring to the reference standard deviation table 112, compares this value with the third reference range, and determines whether maxSD is out of the third reference range. In case of YES, the processing goes to step S45, and in case of NO, the processing goes to step S46.

(Step S45)

Here, the processing of substituting the pixel value of the pixel-of-interest as the pixel value after the filter processing without performing the processing other than the processing of the isotropic area and the processing of the anisotropic area, for example, the filter processing.

(Step S46)

The filter determining unit 11*g* refers to maxSD of the reference standard deviation table 112, and determines whether the direction indicating the maximum value is the direction of FIG. 4(*b*) or not. In case of YES, the processing goes to step S47, and in case of NO, the processing goes to step S48.

(Step S47)

AS in the case of the step S36, the filter setting unit 11*d* sets the anisotropic shape filter along the vertical direction to the anisotropic area of FIG. 4(*b*) with respect to the pixel-of-interest 100, and the filter processor 11*e* performs the median filter processing by using the anisotropic shape filter.

(Step S48 to Step S411)

As in the case of the step S46, in step S48, the filter determining unit 11*g* refers to maxSD of the reference standard deviation table 112, and determines whether the direction indicating the maximum value is the direction of FIG. 4(*c*). In case of YES, the processing goes to step S49, and in case of NO, the processing goes to step S410. The same processing is also executed on the other anisotropic areas.

(Step S412)

It is determined whether the processing on all the pixels of the medical image is finished or not. In case of YES, the processing is finished. In case of NO, the processing returns to step S41.

According to this embodiment, since the maximum value and the direction of the standard deviation are obtained in advance, it is not necessary to calculate the standard deviation in the loop from the step S41 to the step S410, and the processing speed is expected to increase.

Furthermore, the determination as to the anisotropic area processing or the isotropic processing is performed by using the further SD, and thus even when different kinds of images such as a CT image, an MRI image, etc. are read in, a labor of changing the set value for which the CT value or the density value is used can be omitted.

In the foregoing description, from the step S46 to the step S411, the maximum value of the plural standard deviations is searched, and the anisotropic shape filter is set in the vertical direction to the anisotropic area indicating the maximum value. However, as in the case of the first and second embodiments, the minimum value is searched, and the anisotropic shape filter in the same direction as the anisotropic area indicating the minimum value may be set.

<Fifth Embodiment>

Figure 12:
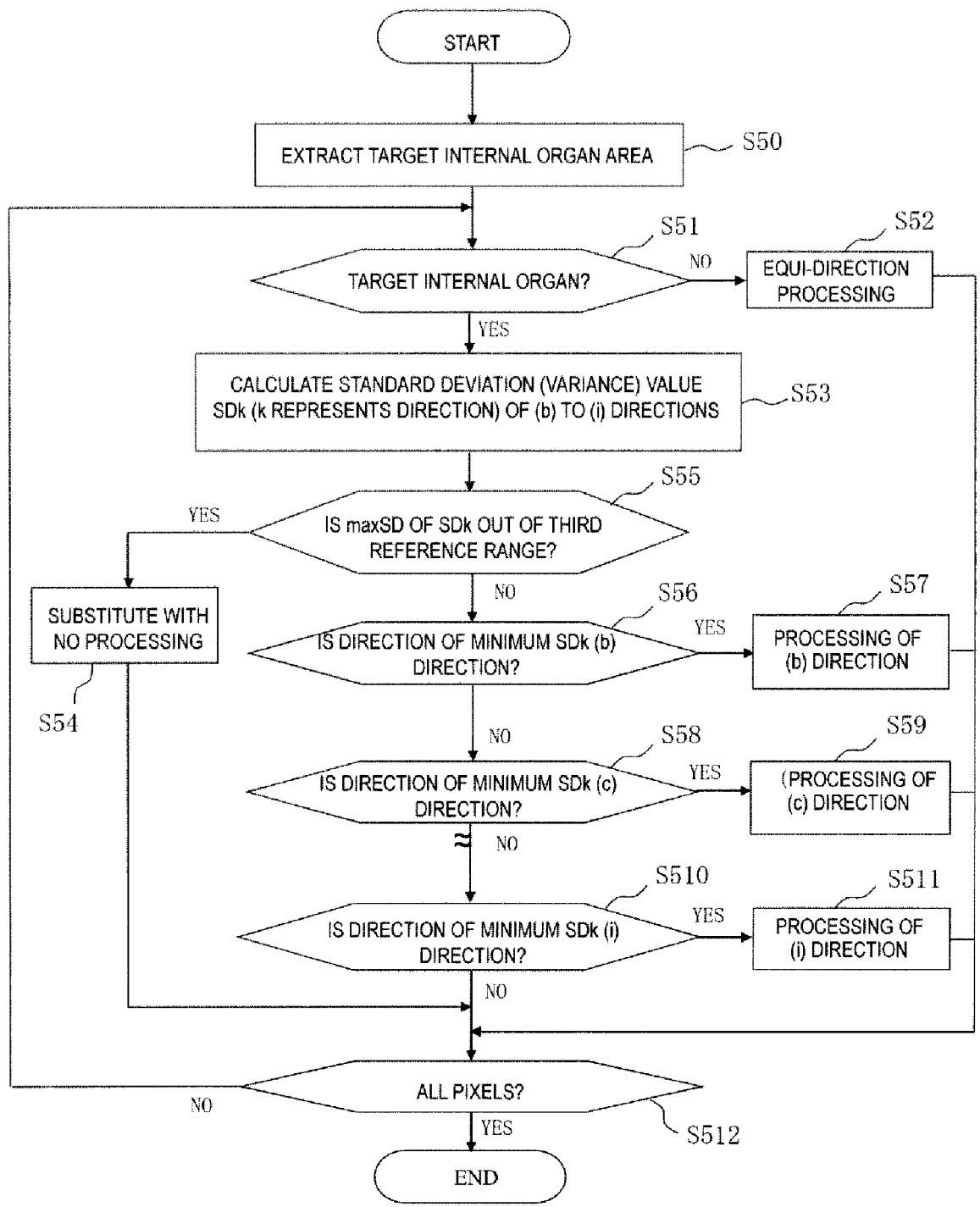
[FIG. 12] is a flowchart showing the flow of processing of a fifth embodiment.

A fifth embodiment is an embodiment of selectively performing the noise reducing processing using the anisotropic area in accordance with the type of an internal organ. The fifth embodiment will be described with reference to FIG. 12. FIG. 12 is a flowchart showing the flow of the processing of the fifth embodiment.

(Step S50)

First, the image reading unit 11*a* reads a CT image. Subsequently, the internal organ extracting unit 11*h* extracts an internal organ area as a noise reducing processing target from the CT image. The extraction of the internal organ area can be performed by subjecting a liver area to binary processing by using CT values corresponding to a liver and performing separating processing from an adjacent internal organ area, for example. When there are plural slices, a liver area is extracted in one slice, and a liver area can be extracted in a slice adjacent to the above slice on the basis of the shape correlation with the previously extracted liver area.

(Step S51)

The filter determining unit 11*g* compares the coordinate of the pixel-of-interest with the coordinate of the target internal organ area extracted by the internal organ extracting unit 11*h*, and determines whether the pixel-of-interest is within the target internal organ area. When the pixel-of-interest is out of the target internal organ area, the process goes to step S52, and when the pixel-of-interest is within the area, the process goes to step S53.

The processing from step S52 to S512 is the same as the processing from the step S11 to step S111 of FIG. 3 according to the first embodiment. The steps from S32 to S311 of the third embodiment may be executed in place of the steps from S11 to S111 of the first embodiment. Furthermore, with respect to the image size, the fifth embodiment may be combined with the second embodiment by combining the enlargement/reduction. Or, by referring to the reference standard deviation table in advance as in the case of the fourth embodiment, the reference standard deviation table may be referred in place of the obtained standard deviation in the processing from step S52 to S512.

According to this embodiment, the noise reducing processing corresponding to the target internal organ can be performed.

<Sixth Embodiment>

Figure 13:
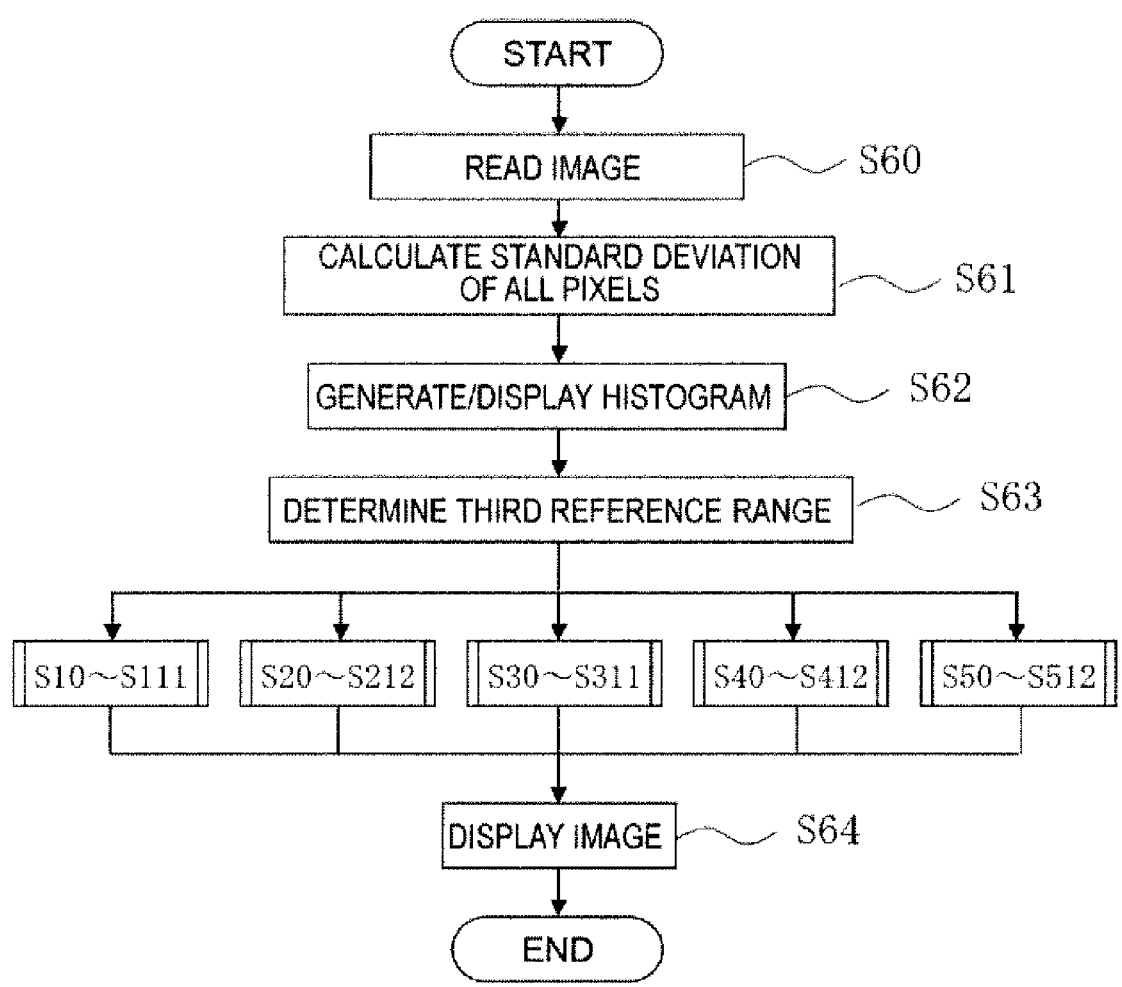
[FIG. 13] is a flowchart showing the flow of processing of a sixth embodiment.

A sixth embodiment is an embodiment in which a third reference range as a reference for determining whether the filter processing using the anisotropic shape filter is performed or not is set by using GUI, and it will be described with reference to the flowchart of FIG. 13. FIG. 13 is a flowchart showing the flow of the processing of the sixth embodiment.

(Step S60)

The image reading unit 11*a* reads an original image including a CT image.

(step S61)

The anisotropic area setting unit 11*b* sets plural anisotropic areas for all pixels of an original image or all pixels within an area which is traced and specified on a medical image through the mouse 16 in advance by a user and on which the user wants to execute the noise reducing processing. The statistical amount calculator 11*c* calculates the standard deviation of each anisotropic area.

For example, when eight anisotropic areas are set per pixel with respect to an image or an indicated area of 100×100 pixels, 80,000 standard deviations are calculated. For example, the standard deviation table 111 of FIG. 11(*a*) is generated, and the calculated standard deviations are temporarily stored in the standard deviation table 111.

(Step S62)

The statistical amount calculator 11c generates the histogram of the calculated standard deviations, and the display control unit 11j displays the histogram of the standard deviations on the monitor 15.

(Step S63)

The user sets the third reference range on the histogram of the standard deviations displayed on the monitor 15. The statistical amount calculator 11c calculates/presents a recommended example of the third reference range. The user may set and input the recommended example as the third reference range, or may finely adjust the recommended example and then set and input it. The reference range setting unit 11k sets the set and input value as the third reference range.

Figure 14:
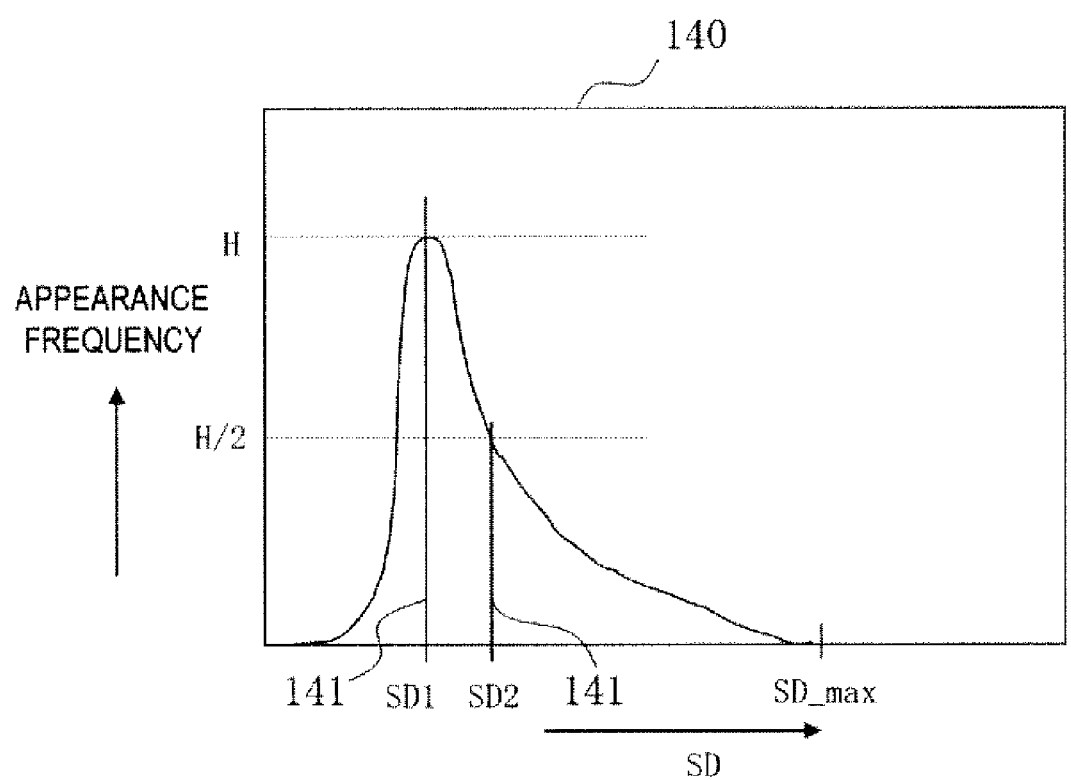
[FIG. 14] is a schematic diagram showing a display example of a histogram of standard deviation.

FIG. 14 is a schematic diagram showing a display example of the histogram of the standard deviations. The statistical amount calculator 11c presents, as the recommended example of the third reference range, a range from a standard deviation SD1 representing the peak value H of a histogram 140 of the standard deviations to a standard deviation SD2 representing the half maximum full-width (½) H of the histogram 140. The third reference range may be set to the ratio to the maximum value SD_max of the standard deviation in the histogram 140 of the standard deviations or the ratio to (SD2−SD1). For example, when the ratio to the SD_max is set to 1/2, SD providing (SD_max))/2 is determined, and when the ratio to SD_max is set to 1/3, SD providing (SD_max)/3 is determined. Furthermore, when the ratio to (ASD2−SD1) is set to 1.5, SD is determined as SD=SD1+1.5(SD2−SD1).

The user can change the third reference range by dragging a bar 141 in the right-and-left direction with the mouse 16.

(Steps S10 to S111, etc.)

Subsequently, any noise reducing processing of the steps S10 to S111, the steps S20 to S211, the steps S30 to S311, the steps S40 to S411 or the steps S50 to S512 is executed.

(Step S63)

The image which has been subjected to the noise reducing processing is displayed, and the processing is finished.

The third reference range is set by using the histogram of the standard deviations, whereby the third reference range can be set in accordance with the amount of the image noise of each image.

<Seventh Embodiment>

Figure 15:
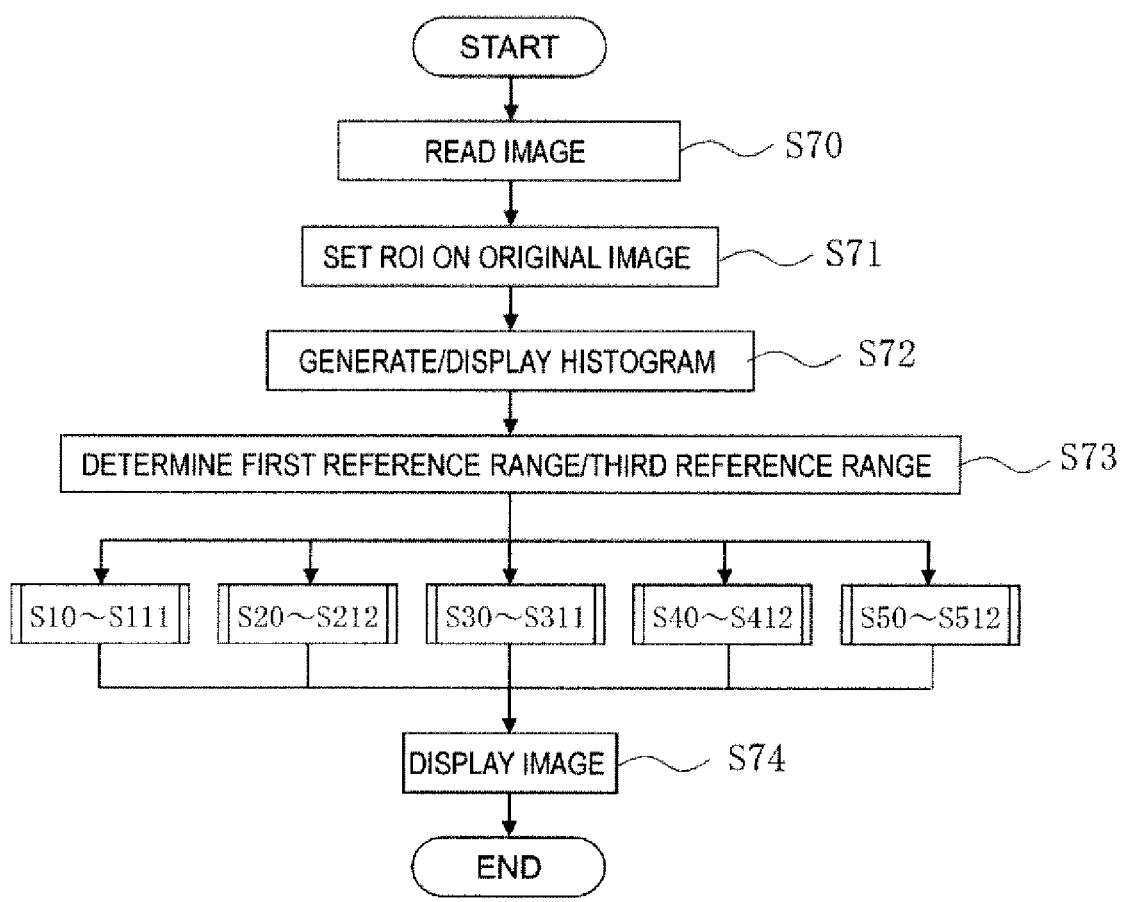
[FIG. 15] is a flowchart showing the flow of processing of a seventh embodiment.

According to a seventh embodiment, the user sets an area-of-interest on an original image, and sets a first reference range and/or a third reference range by using the CT value and the standard deviation of the area-of-interest. The seventh embodiment will be described with reference to FIG. 15. FIG. 15 is a flowchart showing the flow of the processing of the seventh embodiment.

(Step S70)

The image reading unit 11a reads an original image including a CT image.

(Step S71)

The display controller 11j displays an original image 161 on the monitor 15. When the user specifies an area on the original image 161 by the mouse 16, an area-of-interest setting unit 11l sets the indicated area to the area-of-interest (ROI).

(Step S72)

The statistical amount calculator 11c calculates CT values in ROI and the standard deviation of an anisotropic area set in pixels within ROI.

The statistical amount calculator 11c generates a histogram representing the distribution of the CT values within ROI or a histogram representing the distribution of the calculated standard deviations, and the display controller 11j displays it on the monitor 15.

(Step S73)

The user specifies, on the histogram of the CT values displayed on the monitor 15, the first reference range for determining whether the processing using the isotropic shape filter is executed or not. Furthermore, the user specifies, on the histogram of the standard deviations, the third reference range for determining whether the processing using the anisotropic shape filter is executed or not.

The reference range setting unit 11k sets the respective reference ranges according to the specified first reference range and third reference range.

(Steps S10 to S111, etc.)

Subsequently, any noise reducing processing of the steps S10 to S111, the steps S20 to S211, the steps S30 to S311, the steps S40 to S411 or the steps S50 to step S512 is executed.

(Step S74)

The processed image which has been subjected to the noise reducing processing is displayed, and the processing is finished.

Figure 16:
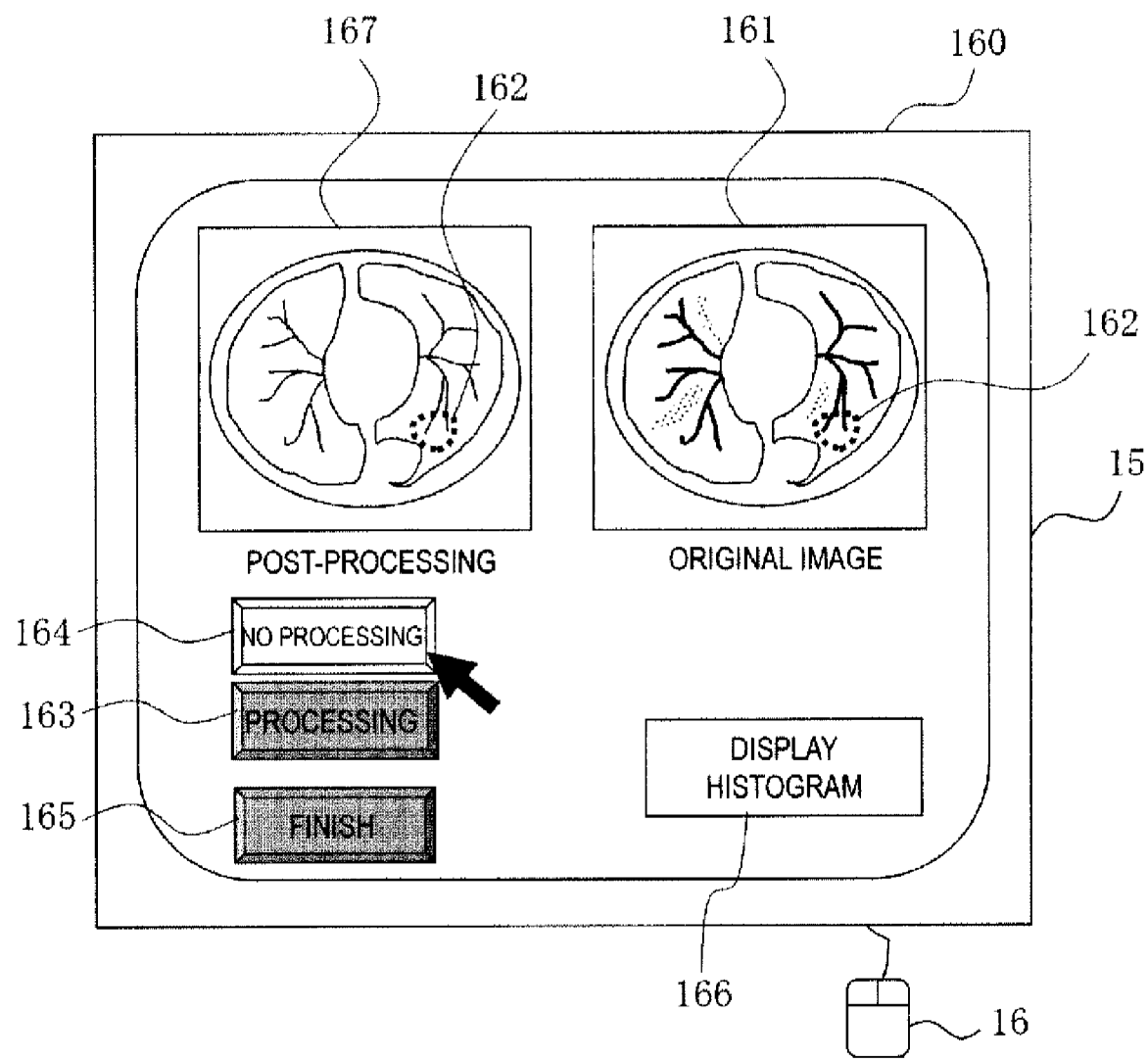
[FIG. 16] is a schematic diagram showing a screen display example used in the seventh embodiment.
Figure 17:
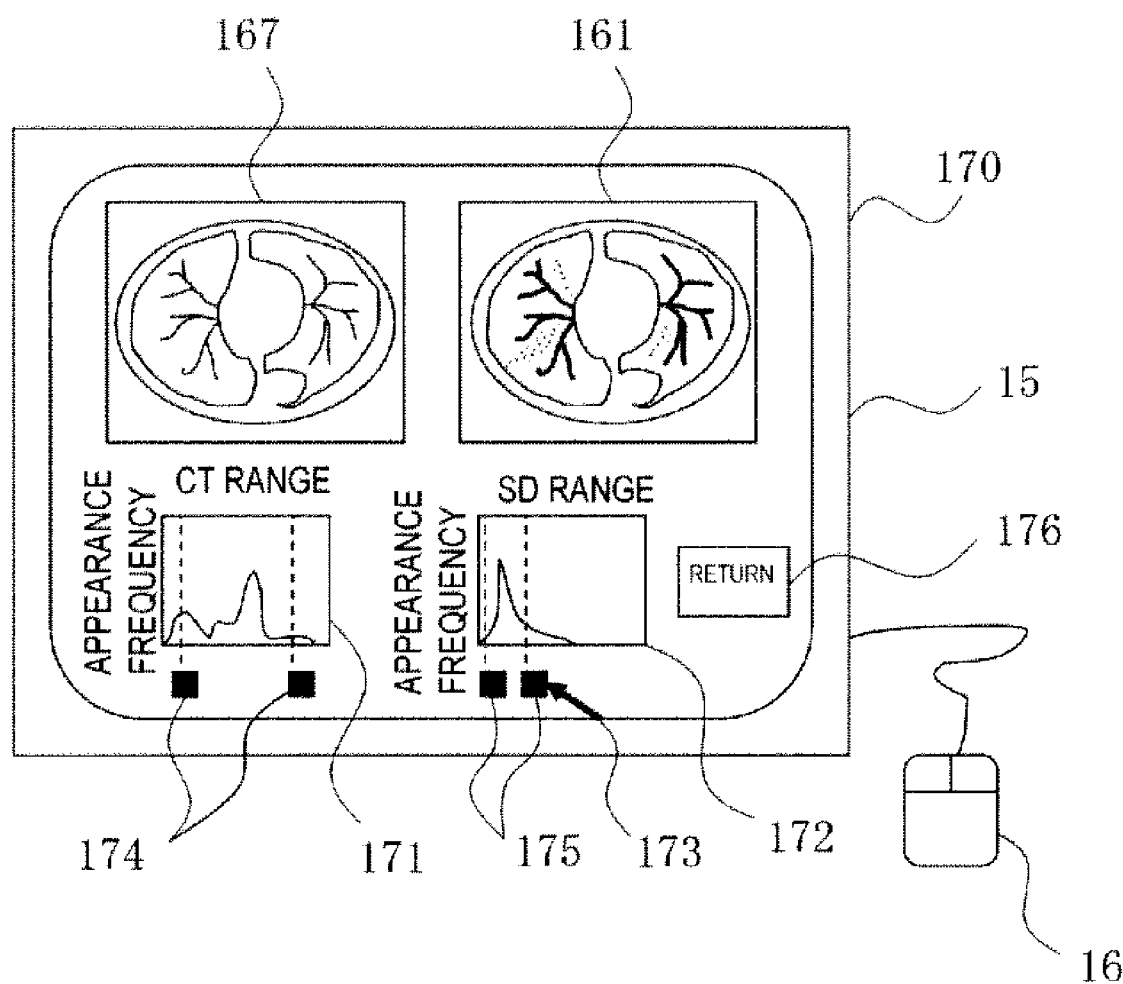
[FIG. 17] is a schematic diagram showing a screen display example used in the seventh embodiment.

FIGS. 16 and 17 are schematic diagrams showing screen display examples of this embodiment.

On a screen 160 of FIG. 16 are displayed the original image 161 including a CT image, an area-of-interest 162 which the user sets on the original image 161 by specifying the area with the mouse 16, soft buttons including a "processing" button 163 with which the area having the CT values and the SD value of the area-of-interest set by the user is set to be within a set value range, a "no processing" button 164 in which the same area is set to be out of the set value range, a "finishing" button 165 for finishing all the processing, and a "histogram display" button 166 for shifting to a histogram display screen (screen 170), and a post-processing image 167 which has been subjected to the noise reducing processing. The post-processing image 167 is displayed in step S74 described later. The area-of-interest 162 set on the original image 161 is drawn on the post-processing image 167 by a dashed line.

The area-of-interest 162 serves to obtain an area for the CT value and the standard deviation to set the reference range. The user sets the area-of-interest 162 on the original image 161. When the user wants to set the value of the area-of-interest 162 as a reference range, the user clicks the "processing" button 163, and when the user does not want to set, the user clicks the "no processing" button 164. In FIG. 16, the "no processing" button 164 is selected, and thus the reference range setting unit 11lk sets the outside ranges of the CT value and standard deviation ranges set in FIGS. 15 and 16 at the outside of the first reference range and the third reference range.

When the user clicks the "histogram display" button 166, the screen shifts from the screen 160 to the screen 170.

On the screen 170 are displayed the original image 161, a CT value histogram 171, a standard deviation histogram 172, an arrow-like pointer 173, a gauge 174 for specifying a CT value range on the CT value histogram 171, a gauge 175 for specifying a SD range on the standard deviation histogram 172, a "return" button 176 for shifting to the screen 160, and the post-processing image 167.

The user operates the pointer 173 by the mouse 16, and specifies the CT value range and the SD range by changing the interval between the gauges 174 or the gauges 175.

The reference range setting unit 11k sets the specified CT value range and SD range to the first reference range and the third reference range, respectively. The post-processing image 167 is also updated in connection with the change of these reference ranges.

According to this embodiment, the reference range to be subjected to the anisotropic processing or the isotropic processing may be set by checking the situation of the noise of the original image or the blood vessel running. Furthermore, the set value can be set by using either the CT value or the standard deviation by displaying the CT value histogram, the standard deviation histogram, the original image and the noise-reduced image in parallel. Therefore, the set value can be estimated while the original image and the noise-reduced image are compared with each other.

<Eighth Embodiment>

Figure 18:
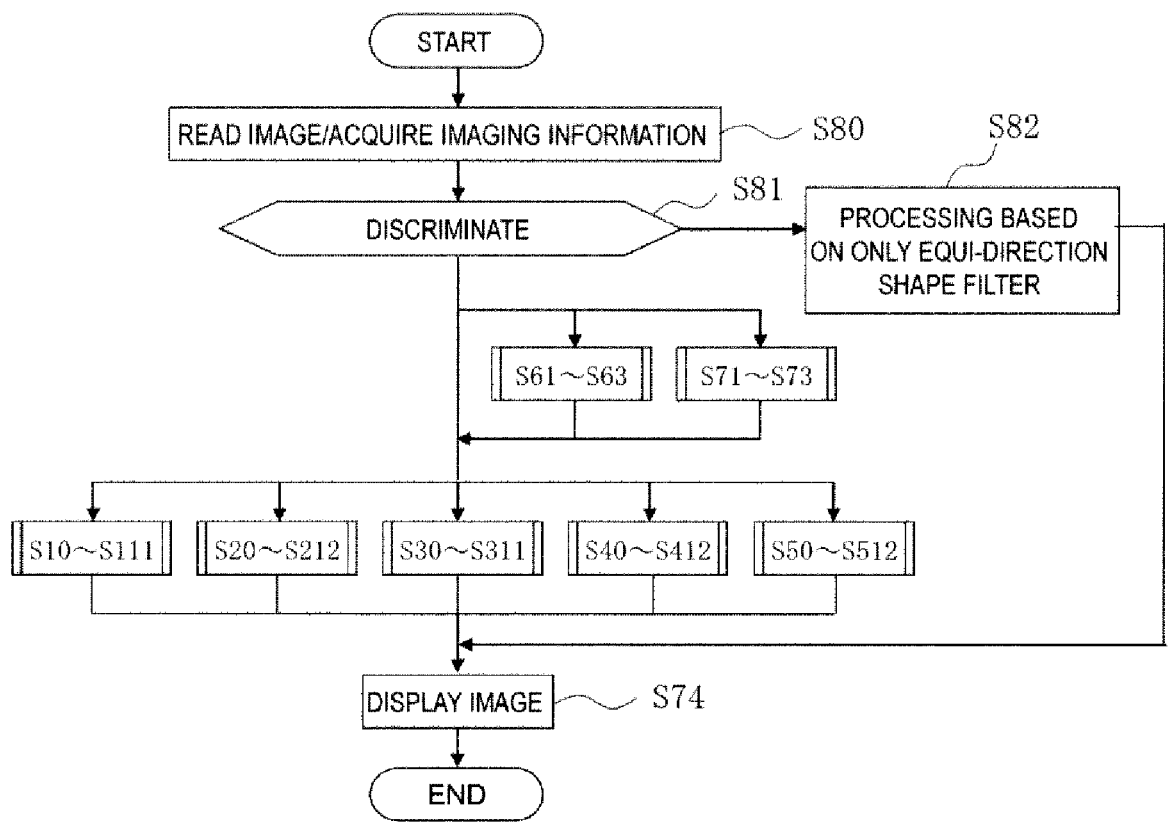
[FIG. 18] is a flowchart showing the flow of processing of an eighth embodiment.

An eighth embodiment is an embodiment for determining on the basis of the imaging condition whether the noise reducing processing according to the present invention is executed or not. The eighth embodiment will be described with reference to FIG. 18. FIG. 18 is a flowchart showing the flow of the processing according to the eighth embodiment.

(Step S80)

The image reading unit 11a reads the original image, and the imaging information acquiring unit 11m acquires imaging information representing the imaging condition under imaging operation from the medical image pickup device 2 or appending information of an image as a processing target. Here, the imaging condition is particularly an imaging condition affecting noise. It is tube current used for the imaging operation in the case of a CT image, it is a value representing strength and weakness of magnetostatic field and/or gradient magnetic field in the case of an MRI image, it is a frequency in the case of a US image, and it is the intensity of X-ray in the case of an X-ray image, for example.

(Step S81)

The image discriminating unit 11n compares the imaging information acquired in step S80 with a reference condition stored in the data storing device 13 in advance, and discriminates a medical image to be processed by using the anisotropic area on the basis of whether the imaging condition is within the reference condition. The reference condition sets an imaging condition range which is estimated to contain relatively large noise, and when the imaging condition satisfies the reference condition, the image is discriminated as an image on which the processing using the anisotropic area should be executed.

Furthermore, the US image has generally a lot of noise as compared with the other kinds of images. Therefore, information representing the type of a medical image may be acquired as the imaging information, "image type: US image" may be set as the reference condition, and the US image may be set to be discriminated as an image on which the processing using the anisotropic area should be executed.

When the imaging condition does not satisfy the reference condition, the processing goes to step S82, and the filter processing based on only the isotropic shape filter is executed.

With respect to the image which is discriminated as the image to be processed by using the anisotropic area by the image discriminating unit 11n, the processing goes to the steps S10 to S111, the steps S20 to S212, the steps S30 to S311, the steps S40 to S412, S50 to S512 or the steps S61 to S63, the steps S71 to S73, and the noise reducing processing using the isotropic area and the anisotropic area is executed. Thereafter, a reverse image is displayed.

According to this embodiment, the noise reducing processing using the anisotropic area can be executed on only the image which is estimated from the imaging condition to have a relatively large amount of noise occurring therein. Therefore, it can be expected that the throughput of the noise reducing processing can be enhanced.

Particularly, when CT images are picked up in group examination, there is a case where imaging is performed while the X-ray dose is made smaller as compared with a case where a CT image for diagnosis is picked up. However, according to this embodiment, when there are CT images having different image noises because the X-ray dose is different between the CT images, the noise reducing processing can be discriminatively used in accordance with the amount of noise of each image.

In the above embodiment, the case where the original image is mainly the CT image. However, when the original image is an MRI image, a US image, or an X-ray image, a density value may be used in place of the CT value.

Furthermore, in the above embodiment, it is described that the processing is executed on one tomogram. However, when the slice thickness is small, the median processing and the smoothing processing over slices may be performed. Accordingly, in this case, an anisotropic area can be set while striding over slices and the number of anisotropic areas set for one pixel-of-interest increases.

DESCRIPTION OF REFERENCE NUMERALS 1 image processing system, 2 medical image pickup device, 3 image database (image DB), 4 LAN, 10 image processing device, 11 CPU, 12 main memory, 13 data storing device, 14 display memory, 15 monitor, 16 mouse, 16a controller, 17 keyboard, 18 network adaptor, 19 bus

The invention claimed is:

1. An image processing device characterized by comprising:
   image reading means that reads a medical image;
   anisotropic area setting means that sets plural anisotropic areas continuous with a pixel of-interest contained in the medical image with the pixel-of-interest being centered;
   statistical amount calculating means that calculates a statistical amount of pixel values of pixels constituting each anisotropic area with respect to each of the plural anisotropic areas;
   filter setting means that determines an anisotropic area having the minimum statistical amount out of the plural anisotropic areas and constructs an anisotropic shape filter in the same direction as the anisotropic area concerned, or determines an anisotropic area having the maximum statistical amount out of the plural anisotropic areas and constructs an anisotropic shape filter by clockwise or counterclockwise rotating the anisotropic area concerned around the pixel-of-interest by 90°, and sets any one of the former anisotropic shape filter and the latter anisotropic shape filter; and
   filter processing means that performs median filter processing or smoothing filter processing by using the anisotropic shape filter.

2. The image processing device according to claim 1, further comprising image size changing means that performs enlarging/reducing an image size of the medical image or an effective field-of-view range of the medical image under arbitrary magnification, wherein the filter setting means calculates a pixel value obtained by interpolating a pixel value of a pixel at an end portion of the anisotropic area and a pixel value of a pixel located within the anisotropic area adjacent to the pixel at the end portion with a coefficient determined in accordance with the arbitrary magnification, and sets an anisotropic shape filter having a shape which is obtained by removing the pixel at the end portion from the anisotropic area, the pixel value of the pixel adjacent to the pixel at the end portion being replaced by the calculated pixel value in the anisotropic shape filter.

3. The image processing device according to claim 1, wherein the medical image is any one of an X-ray CT image, an MRI image, a US image and an X-ray image, there is further provided filter determining means that determines application of an isotropic shape filter having a matrix shape containing the pixel-of-interest located at the center thereof when a CT value or density value of the pixel-of-interest is located at the outside of a first reference range defining a predetermined CT value range or density value range, and when application of the isotropic shape filter is determined, the filter setting means sets the isotropic shape filter in place of the anisotropic shape filter.

4. The image processing device according to claim 1, further comprising:
   internal organ area extracting means that extracts a target internal organ area in the medical image for which a desired internal organ is imaged; and
   filter determining means that determines on the basis of a coordinate of the pixel-of-interest and a coordinate of the target internal organ area whether the pixel-of-interest is contained in the target internal organ area, and determines application of an isotropic shape filter having a matrix shape containing the pixel-of-interest located at the center hereof when the pixel-of-interest is not contained in the target internal organ area, wherein when the application of the isotropic shape filter s determined, the filter setting means sets the isotropic shape filter n place of the anisotropic shape filter.

5. The image processing device according to claim 1, wherein the statistical amount calculating means calculates a further statistical amount with statistical amounts of the plural anisotropic areas set to the pixel-of-interest set as a population, there is further provided filter determining means that determines application of an isotropic shape filter having a matrix shape containing the pixel-of-interest located at the center thereof when the further statistical amount is out of a second reference range defining a predetermined further statistical amount range, and when the application of the isotropic shape filter is determined, the filter setting means sets the isotropic shape filter in place of the anisotropic shape filter.

6. The image processing device according to claim 1, further comprising:
   filter determining means that determines application of an isotropic shape filter having a matrix shape containing the pixel-of-interest located at the center thereof; and
   determining means that determines with respect to a pixel-of-interest determined not to he subjected to the application of the isotropic shape filter by the filter determining means whether a maximum value of the statistical amounts of the plural anisotropic areas calculated for the pixel-of-interest is within a third reference range defining a predetermined range of the statistical amounts,
   wherein when the maximum value of the statistical amounts is determined to be within the predetermined third reference range, the filter setting means sets the anisotropic shape filter.

7. The image processing device according to claim 6, wherein when the maximum value out of the calculated statistical amounts of the plural anisotropic areas is out of the third reference range, the filter setting means substitutes the pixel value of the pixel-of-interest of the medical image as a pixel value of a filter-processed image without setting the anisotropic shape filter.

8. The image processing device according to claim 6, wherein the anisotropic area setting means sets a plurality of the anisotropic areas with respect to each pixel of the medical image, and the statistical amount calculating means calculates statistical amounts of the anisotropic areas set with respect to each pixel of the medical image, and there are further provided histogram display means that generates a histogram of the calculated statistical amounts and displays the histogram, and reference range setting means that sets the third reference range by specifying a desired range on the displayed histogram.

9. The image processing device according to claim 1, further comprising image display means that displays the medical image, and area of-interest setting means for setting an area of interest on the medical image, wherein the statistical amount calculating means comprises histogram display means that generates at least one of a histogram of CT values or density values of pixels constituting the area of interest and a histogram of the statistical amounts of the anisotropic area set to the pixels constituting the area of interest, and displays at least one of the CT value or density value histogram and the statistical amount histogram, and reference range setting means that sets a reference range by setting a desired range on the displayed CT value or density value histogram and the statistical amounts histogram.

10. The image processing device according to claim 1, further comprising acquiring means that acquires imaging information representing an imaging condition of the medical image, and discriminating means that discriminates on the basis of the imaging information a medical image for which the imaging condition satisfies a predetermined condition, wherein the anisotropic area setting means sets the anisotropic area to pixels of the discriminated medical image.

11. An image processing method characterized by comprising:
    a step that reads a medical image;
    a step that sets plural anisotropic areas continuous with a pixel-of-interest contained in the medical image with the pixel-of-interest being centered;
    a step that calculates a statistical amount of pixel values of pixels constituting each anisotropic area with respect to each of the plural anisotropic areas;
    a step that determines an anisotropic area having the minimum statistical amount out of the plural anisotropic areas and constructs an anisotropic shape filter in the same direction as the anisotropic area concerned, or determines an anisotropic area having the maximum statistical amount out of the plural anisotropic areas and constructs an anisotropic shape filter by clockwise or counterclockwise rotating the anisotropic area concerned around the pixel-of-interest by 90°, and sets any one of the former anisotropic shape filter and the latter anisotropic shape filter; and
    a step that performs median filter processing or smoothing filter processing by using the anisotropic shape filter.

12. An image processing program embodied in a non-transitory computer readable medium, the image processing program including instructions executable by a computer to perform a method comprising:
    a step that reads a medical image;
    a step that sets plural anisotropic areas continuous with a pixel-of-interest contained in the medical image with the pixel-of-interest being centered;
    a step that calculates a statistical amount of pixel values of pixels constituting each anisotropic area with respect to each of the plural anisotropic areas;

a step that determines an anisotropic area having the minimum statistical amount out of the plural anisotropic areas and constructs an anisotropic shape filter in the same direction as the anisotropic area concerned, or determines an anisotropic area having the maximum statistical amount out of the plural anisotropic areas and constructs an anisotropic shape filter by clockwise or counterclockwise rotating the anisotropic area concerned around the pixel-of-interest by 90°, and sets any one of the former anisotropic shape filter and the latter anisotropic shape filter; and a step that performs median filter processing or smoothing filter processing by using the anisotropic shape filter.

\* \* \* \* \*